(12) United States Patent
Jorgensen

(10) Patent No.: US 10,899,739 B2
(45) Date of Patent: Jan. 26, 2021

(54) MACROPHAGE MIGRATION INHIBITORY FACTOR INHIBITORS, AND METHODS OF MAKING AND USING SAME

(71) Applicant: YALE UNIVERSITY, New Haven, CT (US)

(72) Inventor: William L. Jorgensen, Deep River, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/186,974

(22) Filed: Nov. 12, 2018

(65) Prior Publication Data

US 2019/0144424 A1 May 16, 2019

Related U.S. Application Data

(60) Provisional application No. 62/586,791, filed on Nov. 15, 2017, provisional application No. 62/710,334, filed on Feb. 16, 2018.

(51) Int. Cl.
| | | |
|---|---|---|
| *C07D 401/14* | (2006.01) | |
| *A61P 37/06* | (2006.01) | |
| *C07D 249/04* | (2006.01) | |
| *C07C 13/16* | (2006.01) | |
| *A61P 35/00* | (2006.01) | |
| *C07D 401/04* | (2006.01) | |

(52) U.S. Cl.
CPC ............ *C07D 401/14* (2013.01); *A61P 35/00* (2018.01); *A61P 37/06* (2018.01); *C07C 13/16* (2013.01); *C07D 249/04* (2013.01); *C07D 401/04* (2013.01)

(58) Field of Classification Search
CPC .................................................. C07D 401/14
See application file for complete search history.

(56) References Cited

U.S. PATENT DOCUMENTS

| | | | | |
|---|---|---|---|---|
| 10,336,721 B2 * | 7/2019 | Jorgensen | ............ | C07D 403/04 |
| 2007/0219189 A1 | 9/2007 | Billich et al. | | |
| 2009/0156588 A1 | 6/2009 | Billich et al. | | |
| 2010/0267714 A1 | 10/2010 | Jorgensen et al. | | |

FOREIGN PATENT DOCUMENTS

| | | |
|---|---|---|
| WO | 2006045505 A1 | 5/2006 |
| WO | 2006108671 A1 | 10/2006 |
| WO | 2016130968 A1 | 8/2016 |

OTHER PUBLICATIONS

Wakefield, Basil "Fluorinated Pharmaceuticals" Innovations in Pharmaceutical Technology 2003, 74, 76-78.*
Asare, et al., "The vascular biology of macrophage migration inhibitory factor (MIF). Expression and effects in inflammation, atherogenesis and angiogenesis", Thromb Haemost. 109(3), Mar. 2013, 391-398 (abstract only).
Bai, et al., "A novel allosteric inhibitor of macrophage migration inhibitory factor (MIF)", J Biol Chem. 287(36), Aug. 2012, 30653-30663.
Conroy, et al., "Inflammation and cancer: macrophage migration inhibitory factor (MIF)—the potential missing link", QJM. 103(11), Nov. 2010, 831-836.
Dawson, et al., "Adding a Hydrogen Bond May Not Help: Naphthyridinone vs Quinoline Inhibitors of Macrophage Migration Inhibitory Factor", ACS Med Chem Lett. 8(12), Nov. 2017, 1287-1291.
Dawson, et al., "Adding a Hydrogen Bond May Not Help: Napthyridinone vs. Quinoline Inhibitors of Macrophage Migration Inhibitory Factor-Supporting Information", ACS Med Chem Lett. 8(12), Nov. 2017, 1287-1291.
Dziedzic, et al., "Design, synthesis, and protein crystallography of biaryltriazoles as potent tautomerase inhibitors of macrophage migration inhibitory factor", J Am Chem Soc. 137(8), Mar. 2015, 2996-3003.
Greven, et al., "Autoimmune diseases: MIF as a therapeutic target", Expert Opin Ther Targets. 14(3), Mar. 2010, 253-264 (abstract only).
Rassaf, et al., "Macrophage migration inhibitory factor in myocardial ischaemia/reperfusion injury", Cardiovasc Res. 102(2), May 2014, 321-328.

* cited by examiner

*Primary Examiner* — David K O'Dell
(74) *Attorney, Agent, or Firm* — Saul Ewing Arnstein & Lehr LLP; Kathryn Doyle; Domingos J. Silva

(57) ABSTRACT

The present invention provides novel inhibitors of MIF tautomerase activity. In certain embodiments, the compounds of the invention are useful in treating or preventing inflammatory and/or auto-immune diseases. In other embodiments, the compounds of the invention are useful in reversing, ameliorating, and/or preventing tumor growth. In yet other embodiments, the compounds of the invention are useful in reversing, ameliorating, and/or preventing angiogenesis.

14 Claims, 9 Drawing Sheets inhibitor 1 (carbon atoms shown in light gray)

MACROPHAGE MIGRATION INHIBITORY FACTOR INHIBITORS, AND METHODS OF MAKING AND USING SAME

CROSS-REFERENCE TO RELATED APPLICATIONS

This application claims priority under 35 U.S.C. § 119(e) to U.S. Provisional Application No. 62/586,791, filed Nov. 15, 2017 and U.S. Provisional Patent Application No. 62/710,334, filed Feb. 16, 2018, all of which applications are hereby incorporated herein by reference in their entireties.

STATEMENT REGARDING FEDERALLY SPONSORED RESEARCH OR DEVELOPMENT

This invention was made with government support under GM032136 awarded by National Institutes of Health. The government has certain rights in the invention.

BACKGROUND OF THE INVENTION

Macrophage migration inhibitory factor (MIF) is a cytokine that plays a central role in numerous inflammatory diseases. MIF is widely expressed in both immune and non-immune cells including macrophages, endothelial cells, and T-cells. Upon activation, the cells release MIF, which promotes the release of other inflammatory cytokines such as TNF-α and IL-1. Excessive or chronic inflammatory response is associated with tissue damage and autoimmune diseases such as rheumatoid arthritis, Crohn's disease, and lupus erythematosus. The connection between inflammatory disease and cancer is also well-established, and MIF has been shown to enhance cell proliferation by inhibiting accumulation of the tumor suppressor p53 and by promotion of angiogenesis. High MIF levels are also associated with numerous neurological disorders, including Alzheimer's disease.

MIF is over-expressed in many cancer cells and can serve as a marker for disease progression. Furthermore, MIF in cancer cells is protected from degradation by Hsp90, which has led to proposed targeting of Hsp90 as an indirect way of inhibiting MIF function. Disruption of the inflammatory cascade and restoration of normal p53 levels have clear implications for the potential therapeutic value of inhibitors of MIF signaling. Indeed, immunoneutralization of MIF or deletion of the MIF gene is known to suppress inflammatory response, tumor growth, and angiogenesis. At the molecular level, what is needed is interference with the interaction between MIF and its cell-surface receptor CD74.

MIF is a toroid-shaped, trimeric protein with a total of 342 amino acid residues. Besides its role as a cytokine, MIF is a keto-enol tautomerase. Though the enzymatic activity appears to be vestigial in humans, there are three tautomerase active sites at the interfaces of the monomer units opening to the outside of the toroid. The presence of the tautomerase sites presents an opportunity for complexation of a tautomerase inhibitor that can also interfere with MIF/CD74 binding.

There is thus a need in the art for identifying novel compounds that inhibit MIF tautomerase activity. In certain embodiments, such compounds can be used to treat inflammatory and/or auto-immune diseases, and reverse, ameliorate and/or prevent tumor growth and angiogenesis. The present invention addresses this need.

BRIEF SUMMARY OF THE INVENTION

The invention provides compound of formula (I), or a salt, solvate, enantiomer, diastereoisomer, geometric isomer, or tautomer thereof:

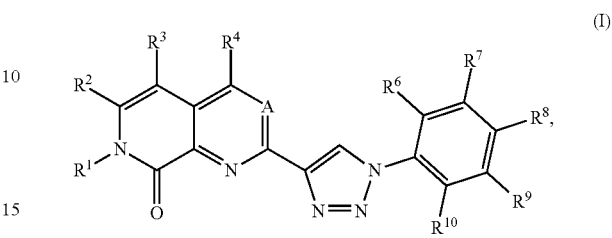

(I)

wherein: A is $CR^5$ or N; $R^1$ is selected from the group consisting of H, $C_1$-$C_6$ alkyl, and $C_1$-$C_6$ heteroalkyl, wherein the alkyl or heteroalkyl group is optionally substituted with at least one selected from the group consisting of —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR; $R^2$ and $R^3$ are independently selected from the group consisting of H, halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, ($C_3$-$C_7$ cycloalkyl)-$C_1$-$C_4$ alkylene, ($C_6$-$C_{10}$ aryl)-$C_1$-$C_4$ alkylene, (5-10 membered heteroaryl)-$C_1$-$C_4$ alkylene, (4-10 membered heterocyclyl)-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR; or one of $R^2$ and $R^3$ is -L-$R^{11}$, wherein: L is selected from the group consisting of a bond, —O—, —N(R)—, $C_1$-$C_4$ alkylene, —C(=O)—, —N(R)C(=O)—, and —C(=O)N(R)—; and $R^{11}$ is optionally substituted phenyl, pyridinyl, or pyrimidinyl; $R^4$, $R^5$, $R^6$, and $R^{10}$ are each independently selected from the group consisting of H, halogen, $C_1$-$C_6$ alkyl, and $C_1$-$C_6$ haloalkyl; $R^7$, $R^8$, and $R^9$ are independently selected from the group consisting of H, halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, ($C_3$-$C_7$cycloalkyl)-$C_1$-$C_4$alkylene, ($C_6$-$C_{10}$ aryl)-$C_1$-$C_4$ alkylene, (5-10 membered heteroaryl)-$C_1$-$C_4$ alkylene, (4-10 membered heterocyclyl)-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR; each occurrence of R is independently selected from the group consisting of H, $C_1$-$C_6$ alkyl, $C_2$-$C_6$ alkenyl, $C_2$-$C_6$ alkynyl, $C_3$-$C_8$ cycloalkyl, or $C_3$-$C_8$ heterocyclyl, or the two R bound to the same N optionally form a $C_3$-$C_8$ heterocyclyl group; each occurrence of R' is independently selected from the group consisting of $C_1$-$C_6$ alkyl, $C_2$-$C_6$ alkenyl, $C_2$-$C_6$ alkynyl, $C_3$-$C_8$ cycloalkyl, or $C_3$-$C_8$ heterocyclyl; each alkyl, alkenyl, alkynyl, cycloalkyl, or heterocyclyl group is optionally substituted with at least one substituent selected from the group consisting of halogen, $C_6$-$C_{10}$ aryl, 5-10 membered heteroaryl, 4-10 membered heterocyclyl, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR; and each phenyl or heteroaryl group is optionally substituted with at least one substituent selected from the group consisting of halogen, C$_1$-C$_6$ alkyl, C$_2$-C$_6$ alkenyl, C$_2$-C$_6$ alkynyl, C$_3$-C$_7$ cycloalkyl, C$_6$-C$_{10}$ aryl, 5-10 membered heteroaryl, 4-10 membered heterocyclyl, C$_3$-C$_7$ cycloalkyl-C$_1$-C$_4$ alkylene, C$_6$-C$_{10}$ aryl-C$_1$-C$_4$ alkylene, 5-10 membered heteroaryl-C$_1$-C$_4$ alkylene, 4-10 membered heterocyclyl-C$_1$-C$_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR.

In certain embodiments, the compound is a compound of formula (Ia):

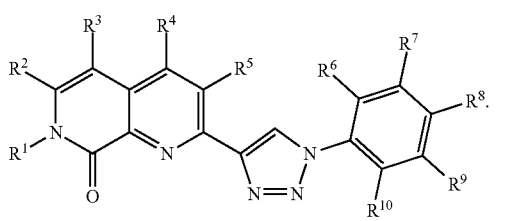

In certain embodiments, the compound is a compound of formula (Ib):

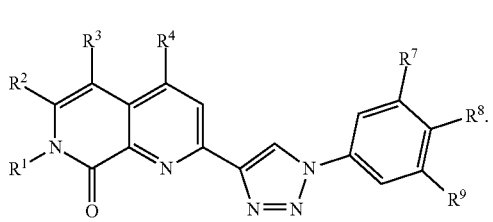

In certain embodiments, the compound is a compound of formula (Ic):

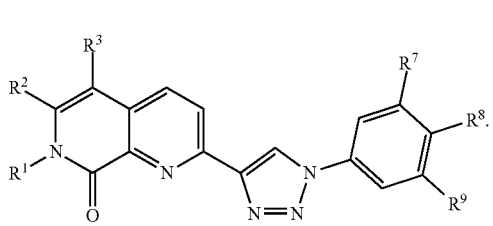

In certain embodiments, the compound is a compound of formula (Id):

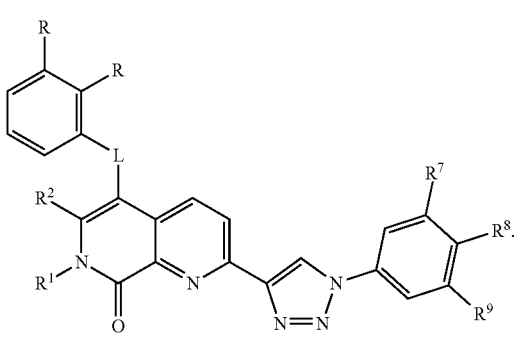

In certain embodiments, R$^1$ is selected from the group consisting of H, —CH$_3$, —CH$_2$CH$_2$OH, —CH$_2$CH$_2$NH$_2$, —CH$_2$CH$_2$OCH$_2$CH$_2$OH, —CH$_2$CH$_2$OCH$_2$CH$_2$NH$_2$, —CH$_2$CH$_2$OCH$_2$CH$_2$-4-morpholinyl, —CH$_2$COOH, —CH$_2$CH$_2$COOH, and —CH$_2$CH$_2$CH$_2$COOH. In certain embodiments, R$^1$ is not —CH$_3$ or —CH$_2$COOH.

In certain embodiments, R$^2$ is H or —OR.

In certain embodiments, R$^3$ is selected from the group consisting of H, C$_6$-C$_{10}$ aryl, and —OR. In certain embodiments, R$^3$ is H, unsubstituted phenyl, or phenyl substituted with 1 substituent selected from the group consisting of C$_1$-C$_6$ alkyl, halogen, C$_1$-C$_6$ alkoxy, and —OR", wherein R" is unsubstituted phenyl or phenyl substituted with 1 group independently selected from the group consisting of —OR and —C(=O)OR.

In certain embodiments, one of R$^2$ and R$^3$ is -L-R$^{11}$.

In certain embodiments, L is O or NH.

In certain embodiments, R$^2$ and an optional substituent in R$^{11}$ are independently selected from the group consisting of H, C$_1$-C$_6$ alkoxy, C$_1$-C$_6$ alkoxy-C$_1$-C$_6$ alkyl, carboxy, carboxy-C$_1$-C$_6$ alkyl, amino-C$_1$-C$_6$ alkyl, C$_1$-C$_6$ alkylamino-C$_1$-C$_6$ alkyl, di(C$_1$-C$_6$ alkyl)amino-C$_1$-C$_6$ alkyl, amino-C$_1$-C$_6$ alkoxy-C$_1$-C$_6$ alkyl, C$_1$-C$_6$ alkylamino-C$_1$-C$_6$ alkoxy-C$_1$-C$_6$ alkyl, di(C$_1$-C$_6$ alkyl)amino-C$_1$-C$_6$ alkoxy-C$_1$-C$_6$ alkyl, 4-10 membered heterocyclyl-C$_1$-C$_6$ alkyl, 4-10 membered heterocyclyl-C$_1$-C$_6$ alkoxy-C$_1$-C$_6$ alkyl, C$_1$-C$_6$ alkoxy-C$_1$-C$_6$ alkoxy, amino-C$_1$-C$_6$ alkoxy, C$_1$-C$_6$ alkylamino-C$_1$-C$_6$ alkoxy, di(C$_1$-C$_6$ alkyl)amino-C$_1$-C$_6$ alkoxy, amino-C$_1$-C$_6$ alkoxy-C$_1$-C$_6$ alkoxy, C$_1$-C$_6$ alkylamino-C$_1$-C$_6$ alkoxy-C$_1$-C$_6$ alkoxy, di(C$_1$-C$_6$ alkyl)amino-C$_1$-C$_6$ alkoxy-C$_1$-C$_6$ alkoxy, 4-10 membered heterocyclyl-C$_1$-C$_6$ alkoxy, 4-10 membered heterocyclyl-C$_1$-C$_6$ alkoxy, carboxy-C$_1$-C$_6$ alkoxy, carboxy-C$_1$-C$_6$ alkyl-C$_1$-C$_6$ alkoxy, and carboxy-C$_1$-C$_6$ alkoxy-C$_1$-C$_6$ alkoxy.

In certain embodiments, R$^4$ and R$^5$ are independently selected from the group consisting of H and C$_1$-C$_6$ alkyl. In certain embodiments, R$^4$ and R$^5$ are independently selected from the group consisting of H, F, methyl, and ethyl.

In certain embodiments, R$^6$ is H; R$^7$ is halogen, C$_1$-C$_6$ alkyl, or —OR; R$^8$ is —OH, halogen, —CN, —OR, —NRR, or —C(=O)NRR; R$^9$ is H or halogen; and R$^{10}$ is H. In certain embodiments, R$^6$, R$^7$, R$^9$, and R$^{10}$ are each independently selected from the group consisting of H and F.

In certain embodiments, R$^8$ is selected from the group consisting of H, F, Cl, and —OH.

The invention further provides a pharmaceutical composition comprising at least one compound of the invention and at least one pharmaceutically acceptable excipient.

The invention further provides a method of inhibiting macrophage migration inhibitory factor (MIF) activity in a subject. The invention further provides a method of treating a disease or condition in which inhibition of macrophage migration inhibitory factor (MIF) activity in a subject is therapeutically beneficial. The invention further provides a method of treating an inflammatory disease or condition in a subject. The invention further provides a method of treating an autoimmune disease in a subject. The invention further provides a method of treating cancer in a subject. The invention further provides a method of treating a disease or condition associated with high MIF expression in a subject. The invention further provides a method of treating anemia of chronic disease in a subject.

In certain embodiments, the method comprises administering to the subject a therapeutically effective amount of a compound of the invention, or a pharmaceutically acceptable salt or solvate thereof.

In certain embodiments, the compound is formulated as a pharmaceutical composition further comprising at least one pharmaceutically acceptable excipient.

In certain embodiments, the inflammatory disease or condition is selected from the group consisting of proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type 1 diabetes, type 2 diabetes, Berger's disease, Retier's syndrome, and Hodgkin's disease.

In certain embodiments, the autoimmune disease is selected from the group consisting of multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome, and autoimmune inflammatory eye disease.

In certain embodiments, the cancer is a solid tumor or a hematological cancer.

In certain embodiments, the cancer is selected from the group consisting of prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, lymphoma, leukemia, diffuse large B-cell lymphoma (DLBCL), mantle cell lymphoma, non-Hodgkin's lymphoma, Hodgkin's lymphoma, and multiple myeloma.

In certain embodiments, the disease or condition associated with high MIF expression is selected from the group consisting of protozoal infection, fungal infection, bacterial infection, viral infection, anemia of chronic disease, asthma, and autism spectrum disorder (ASD).

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

DETAILED DESCRIPTION OF THE INVENTION

The present invention relates in part to the discovery of novel inhibitors of MIF tautomerase activity. In certain embodiments, the compounds of the invention are useful in treating or preventing inflammatory and/or auto-immune diseases. In other embodiments, the compounds of the invention are useful in reversing, ameliorating, and/or preventing tumor growth. In yet other embodiments, the compounds of the invention are useful in reversing, ameliorating, and/or preventing angiogenesis.

Potent MIF tautomerase inhibitors have been previously identified based on computer-aided design, small molecule synthesis, inhibition and binding assays, and protein crystallography. In certain embodiments, 4-quinolinyl-triazoles with $K_i$ values in the tautomerase assay below 50 nM have been identified (see, for example, WO 2016/130968 A1), and the compound activities were confirmed by $K_d$ measurements in a fluorescence polarization assay (see also Dziedzic, et al., 2015, J. Am. Chem. Soc. 137:2996-3003; Cisneros, et al., 2016, J. Am. Chem. Soc. 138:8630-8638; Cisneros, et al., 2017, ACS Med. Chem. Lett. 8:124-127). In addition, crystal structures were reported for complexes of three of the inhibitors with MIF including for the parent 1 (R=H) and its methoxyethoxy analog, 1 (R=MOEO).

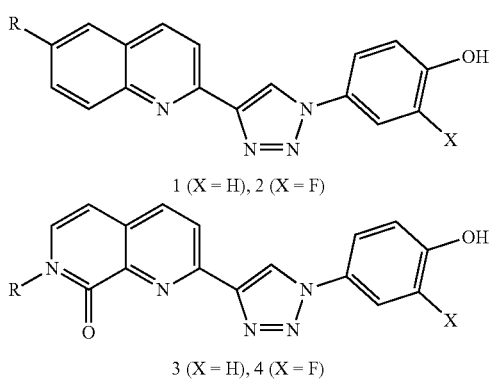

1 (X = H), 2 (X = F)

3 (X = H), 4 (X = F)

Figure 1:
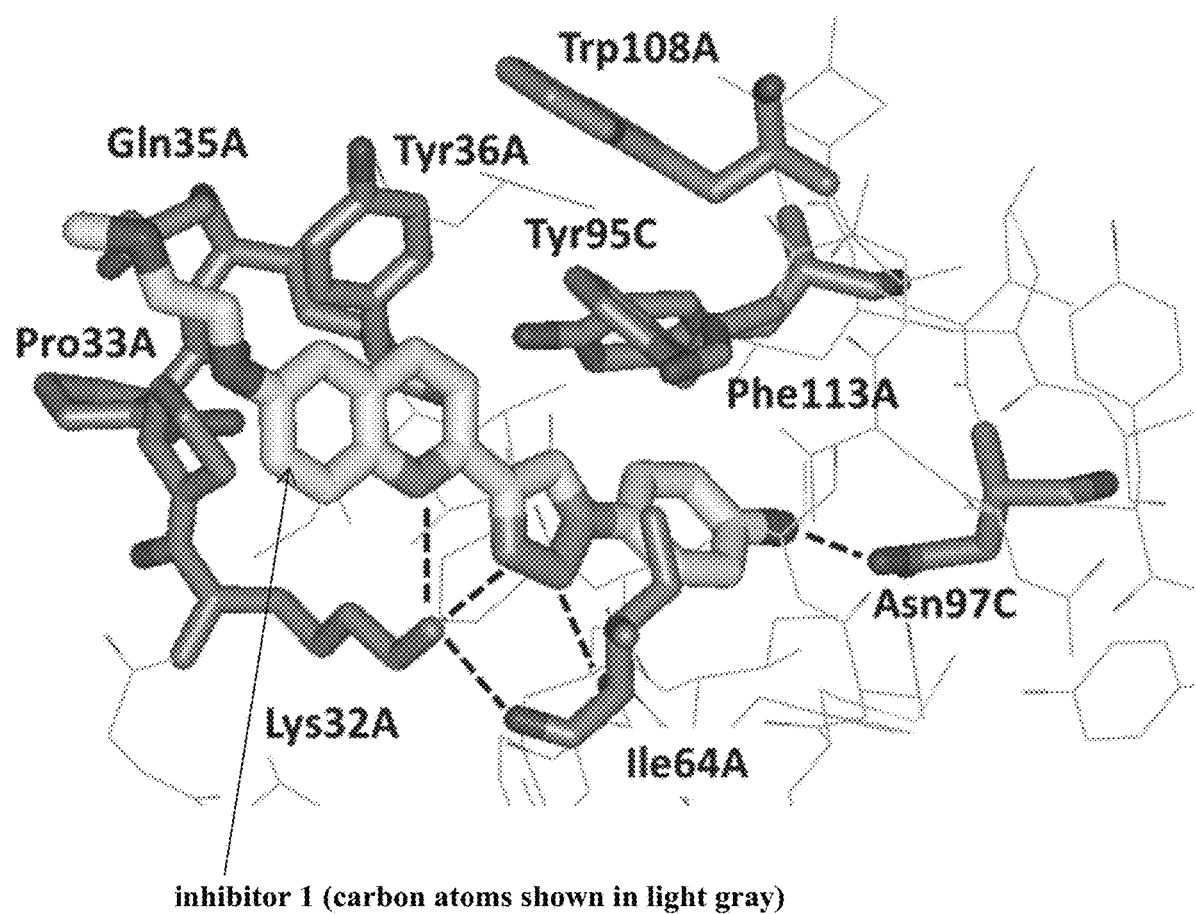
FIG. 1 illustrates a rendering from the 1.8 Å crystal structure of 1 (R=MOEO) bound to MIF (PDB ID: 4WRB). Hydrogen bonds are highlighted with dashed lines; the methoxyethoxy group on C6 of the quinoline is solvent-exposed.
Figure 2:
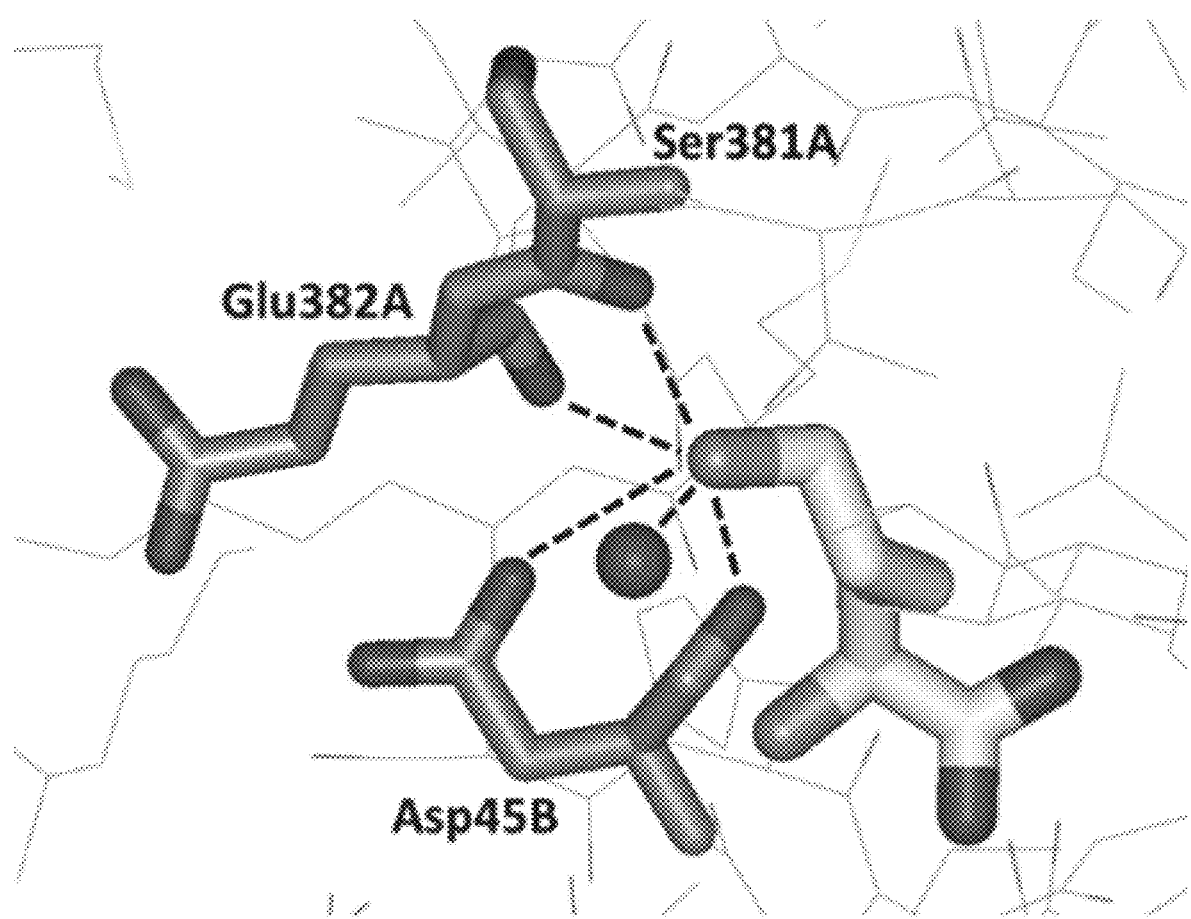
FIG. 2 illustrates coordination of a lysine ligand in the crystal structure of a complex with an aspartate kinase (PDB ID: 3AB4). Hydrogen bonds are denoted with dashed lines; the O—N distances going counterclockwise from the top are 2.58, 3.43, 3.51, 2.74, and 2.61 Å.

The positioning of the latter compound in the MIF tautomerase site is illustrated in FIG. 1. In addition to aryl-aryl interactions with Tyr36, Tyr95, and Phe113, hydrogen bonds occur between Asn97 and the phenolic hydroxyl group of the inhibitor, the backbone NH of Ile64 and N2 of the triazole, and the ammonium group of Lys32 with N3 of the triazole, the quinoline nitrogen, and the carbonyl oxygen of Ile64. The triple coordination of Lys32 is striking and can be expected to be augmented by one or two water molecules as the Lys32-Gln35 segment is on the surface of the protein. This follows from prior computations of the hydration of methylammonium ion, which reveal four to five hydrogen bonds with water molecules (Jorgensen & Gao, 1986, J. Phys. Chem. 90:2174-2182), and from viewing numerous crystal structures in the RSCB Protein Data Bank. The ammonium group of lysine in certain embodiments participates in a total of four or five hydrogen bonds with surrounding residues, ligands, and water molecules. A sample illustration is provided in FIG. 2 from a crystal structure for an aspartate kinase with lysine itself as a ligand (Yoshida, et al., 2010, J. Biol. Chem. 285:27477-27486). The ammonium group is seen to engage in five hydrogen bonds with three backbone carbonyl groups, the side-chain carboxylate group of an aspartate residue, and a water molecule.

Figure 3:
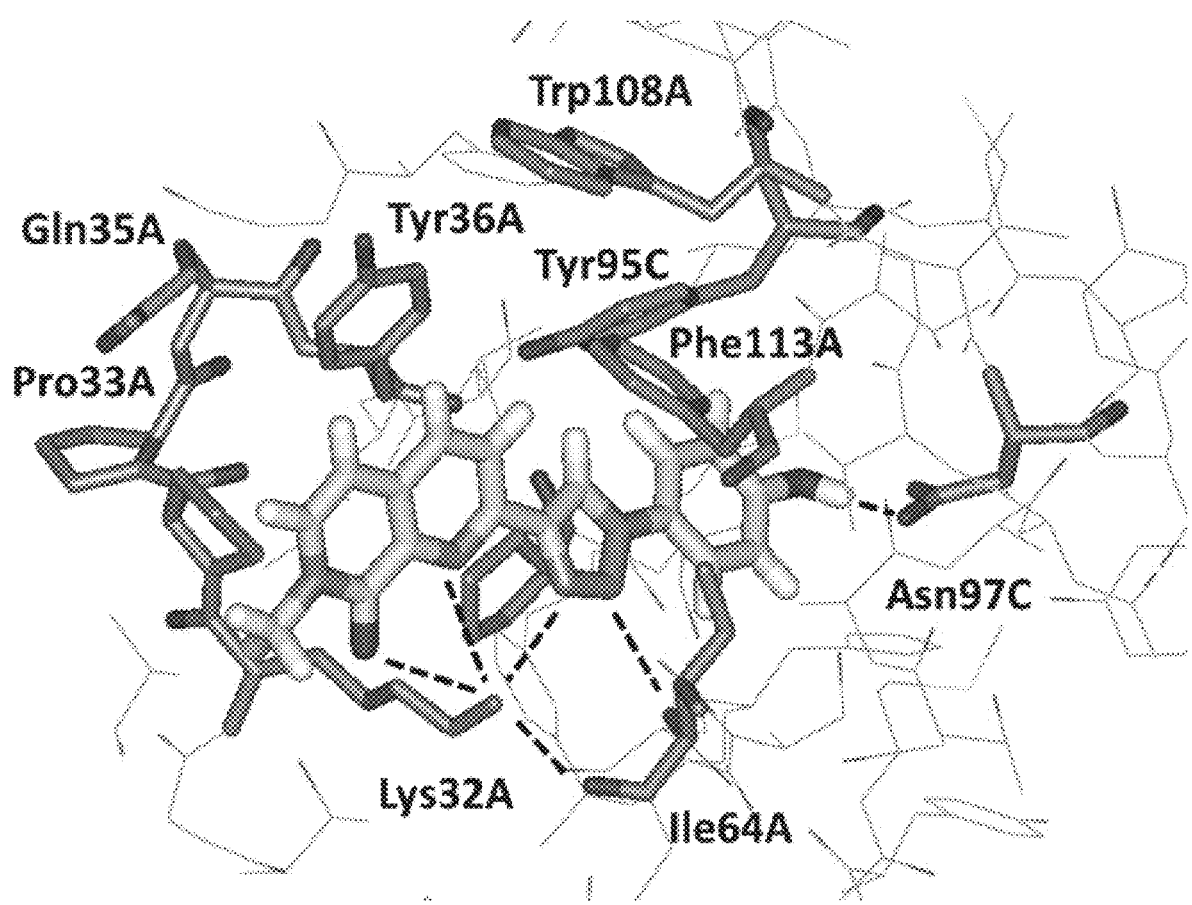
FIG. 3 illustrates a modeled complex of 3a (carbon atoms in light gray) with MIF using the BOMB program. Hydrogen bonds are shown with dashed lines.
Figure 4A:
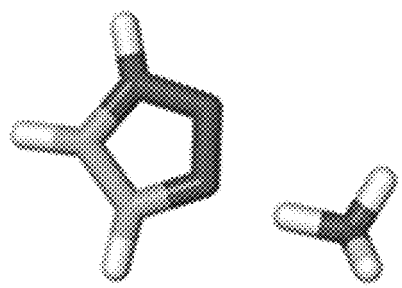
FIGS. 4A-4C illustrate computed structures for complexes of ammonium ion with (FIG. 4A) 1,2,3-triazole and its (FIG. 4B) quinolinyl and (FIG. 4C) 1,7-naphthyridin-8-onyl analogs. Gas-phase DFT results give interaction energies of −36, −45, and −59 kcal/mol for FIG. 4A, FIG. 4B, and FIG. 4C.
Figure 4B:
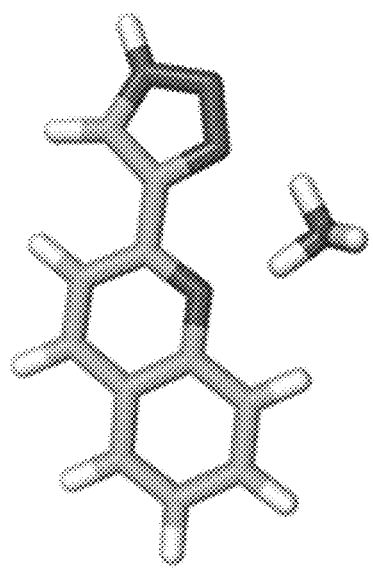
Figure 4C:
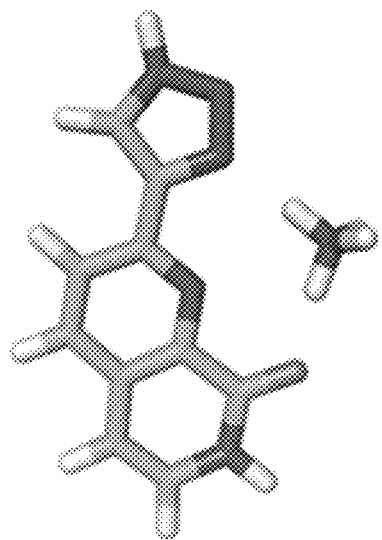

In view of this pattern, modifications of 1 were sought featuring additional coordination of Lys32 that could enhance the inhibition of MIF's tautomerase activity. Addition of a phenoxy group at C8 in the quinoline led to a five-fold reduction in the inhibitory activity compared to the parent 1 (R=H). Substitution of a 4-methoxyphenyl group at C8 to engage in a cation-π interaction with Lys32 was even less successful, while replacement of the quinoline with 1,8-naphthyridine resulted in a 2.5-fold reduction in potency. In certain embodiments, placement of a carbonyl group at C8 of the quinoline can project closer to Lys32 than N8 of the naphthyridine. Thus, 1,7-naphthyridin-8-ones as in 3 and 4 were prepared. Model building with the BOMB program (Jorgensen, 2009, Acc. Chem. Res. 42:724-733) using OPLS force fields (Jorgensen & Tirado-Rives, 2005, Proc. Natl. Acad. Sci. U.S.A. 102:6665-6670) provided auspicious images as in FIG. 3 for the complex of 3a (3, R=Me) with MIF. The computed structure has hydrogen bonds between Lys32 and the naphthyridinone 0 and N, N3 of the triazole, and the carbonyl group of Ile64 with lengths of 3.29, 3.33, 3.18, and 2.76 Å, respectively. DFT calculations (B2PLYP-D3BJ/aug-cc-pVTZ//ωB97X-D/6-311G++ (d,p)) (Goerigk & Grimme, 2011, Phys. Chem. Chem. Phys. 13:6670-6688; Frisch, et al., Gaussian 09, revision D.01; Gaussian, Inc.: Wallingford, C T, 2009) were also carried out for model complexes of $NH_4^+$ with 1,2,3-triazole and the quinolinyl and naphthyridinonyl the three complexes. Effects of hydration were then approximated using a polarizable continuum model (IEFPCM) (Cancès, et al., 1997, J. Chem. Phys. 107:3032-3041), yielding interaction energies of −9.9, −11.7, and −17.6 kcal/mol. Monte Carlo free-energy perturbation (FEP) calculations were also run at 25° C. for the conversion of 3a to 1a (1, R=H) in TIP4P water both unbound and bound to MIF using standard protocols (Dziedzic, et al., 2015, J. Am. Chem. Soc. 137:2996-3003), including the OPLS-AA/M force field for MIF and OPLS/CM1A for the inhibitors (Jorgensen & Tirado-Rives, 2005, Proc. Natl. Acad. Sci. U.S.A. 102:6665-6670; Robertson, et al., 2015, J. Chem. Theory Comput. 11:3499-3509). The FEP calculations were run twice with somewhat different initial geometries for the complex; the two results both predict a slightly more favorable free energy of binding for 3a by 0.28±0.32 and 0.45±0.32 kcal/mol. Without wishing to be limited by any theory, such differences are too small to translate into a clear experimental effect.

Scheme 1. Synthesis of Acetylenic Intermediates.

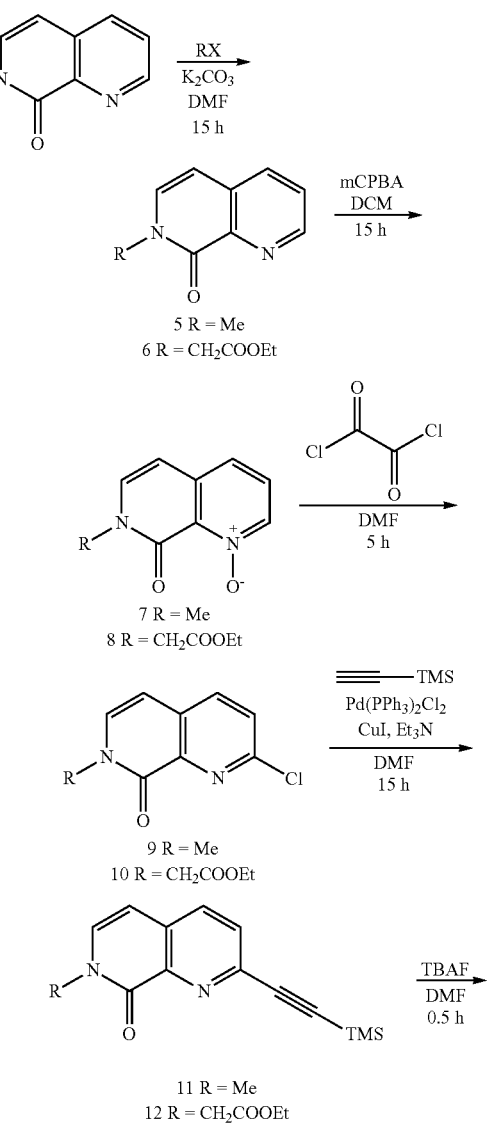

5 R = Me
6 R = $CH_2COOEt$

7 R = Me
8 R = $CH_2COOEt$

9 R = Me
10 R = $CH_2COOEt$

11 R = Me
12 R = $CH_2COOEt$

-continued

13 R = Me
14 R = CH$_2$COOEt 3 and 4 with R=Me (3a, 4a) and CH$_2$COOH (4b) were synthesized. The key intermediates are the acetylenes 13/14 in Scheme 1, which are converted to the desired products via one-pot Cu(I)-catalyzed click reactions. Starting from commercially available 1,7-naphthyridin-8(7H)-one, alkylation with methyl iodide or ethyl-2-bromoacetate provides 5/6, which after mCPBA oxidation and treatment with oxalyl dichloride yields the 2-chloro-naphthyridinones 9/10. A Sonogashira coupling followed by removal of the TMS protecting group delivers the desired compounds 13/14. For 4b, the ethyl ester was hydrolyzed with NaOH in dioxane as the final step.

Figure 5:
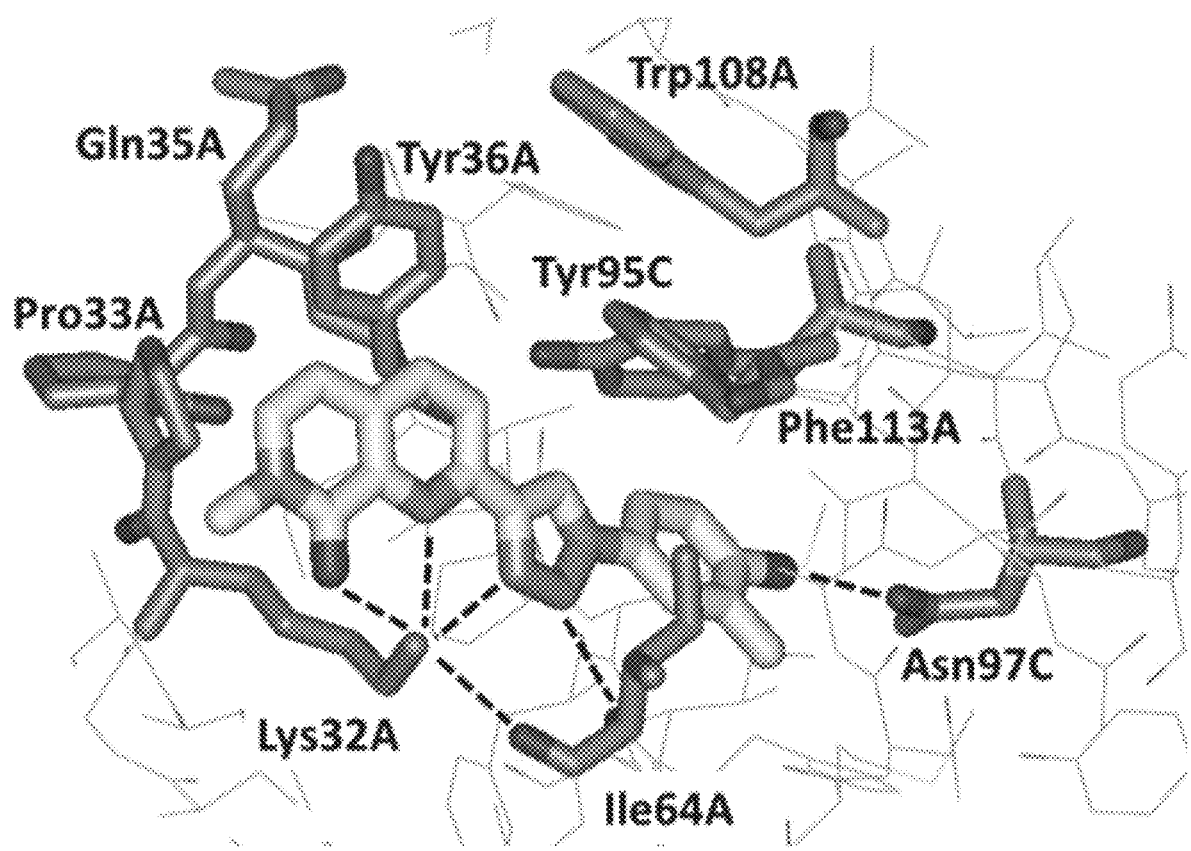
FIG. 5 illustrates a rendering from the 2.16 Å crystal structure of 4a (carbon atoms in light gray) bound to MIF (PDB ID: 6B1C).

Cocrystal structures for 3a, 4a, and 4b bound to MIF were obtained at resolutions of 1.17, 2.16, and 2.00 Å. The structures are all similar for the binding sites; for 4a, FIG. 5 illustrates the four expected hydrogen bonds to Lys32. The structures for 4a and 4b also confirm that the fluorine atom points between Ile64 and Asn97. In the 1.17 Å structure for 3a, all three binding sites for the MIF trimer are occupied. In one copy, the O -Lys N or N-Lys N distances are 2.94, 3.16, 2.95, and 2.82 Å for the naphthyridinone 0 and N, triazole N, and Ile64 oxygen atom, and in the other copies, they are 2.83, 3.13, 3.03, 2.80 Å and 3.04, 3.23, 3.03, 3.34 Å. Thus, there are small differences associated with variations in the interprotein packing. No hydrogen-bonded water molecules are resolved for Lys32, while there is one 2.83 Å from the naphthyridinone oxygen atom.

For the assaying, inhibition constants K$_i$ were determined as before using 4-hydroxyphenylpyruvic acid (HPP) as the substrate (Cisneros, et al., 2016, Bioorg. Med. Chem. Lett. 26:2764-2767). Inhibitory activity is monitored by measuring formation of the borate complex of the enol product at 305 nm using a Tecan Infinite F500 plate reader. Binding constants K$_d$ were also obtained for the new compounds using a fluorescence polarization assay (Cisneros, et al., 2016, J. Am. Chem. Soc. 138:8630-8638). In addition, the aqueous solubility of 4b was measured with a shake-flask procedure (Cisneros, et al., 2017, ACS Med. Chem. Lett. 8:124-127). Saturated solutions in Britton-Robinson buffer (pH 6.5) are filtered (Acrodisc syringe, 0.2 µm pore) and analyzed by UV-vis spectroscopy (Agilent 8453).

The assay results for the naphthyridinones are compared with data for previously reported analogs of 1 and 2 and a reference compound, ISO-1 (methyl 3-(4-hydroxyphenyl)-4,5-dihydroisoxazole-5-carboxylate; Lubetsky, et al., 2002, J. Biol. Chem. 277:24976-24982), in Table 1. For ISO-1, K$_i$ measurements were made nine times with results of 21-39 µM and an average of 30 µM, while K$_d$ measurements were made four times with results of 20-30 µM, averaging 23 µM. The K$_i$ and K$_d$ results in Table 1 are in good accord with the differences, consistent with the expected uncertainties for both measurements.

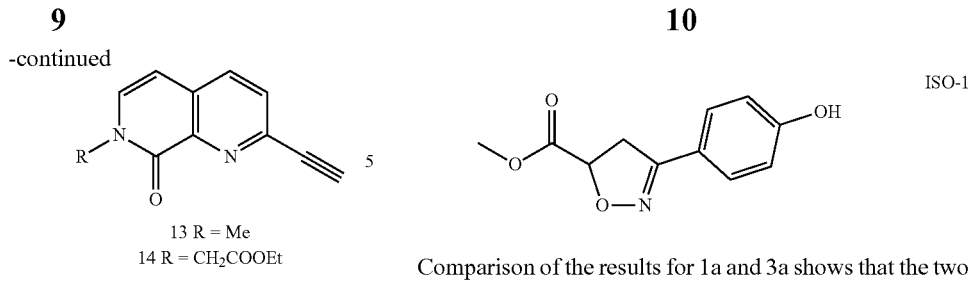

Comparison of the results for 1a and 3a shows that the two compounds have essentially the same activity. Though 3a represents an improvement over the previous modifications of the quinoline fragment, it is provocative in view of the added hydrogen bond to Lys32 that is well-documented in the crystal structures. Other analogs of 1a also typically have K$_i$ and K$_d$ values between 0.2 and 0.4 µM (Table 1). Addition of the fluorine in progressing from 1 to 2 usually improves activity two- to four-fold, as for 1d, 1e, and if vs. 2a, 2b, and 2c. Without wishing to be limited by any theory, the effect is attributed to enhanced strength of the hydrogen bond between the phenolic hydroxyl group and Asn97 as well as hydrophobic contact of the fluorine with the side chain of Met101. The five-fold enhancement in Ki and two-fold enhancement in Kd for 3a vs. 4a suggests that the K$_i$ listed for 3a in Table 1 may be somewhat higher than its actual value. In any event, 4a and 4b are very potent MIF tautomerase inhibitors with K$_i$s of 75 and 90 nM. These activities are again similar to those for analogs of 2 in spite of the added hydrogen bond with Lys32 (FIG. 5). The carboxylic acid 4b was chosen for synthesis since there seemed to be a pattern favoring expected placement of the carboxylate group near Lys32 as in 2c and 2d vs 2a and 2b; however, the electrostatic benefit is not apparent for 4a vs 4b, perhaps owing to the proximity of the naphthyridinone carbonyl group.

Figure 6:
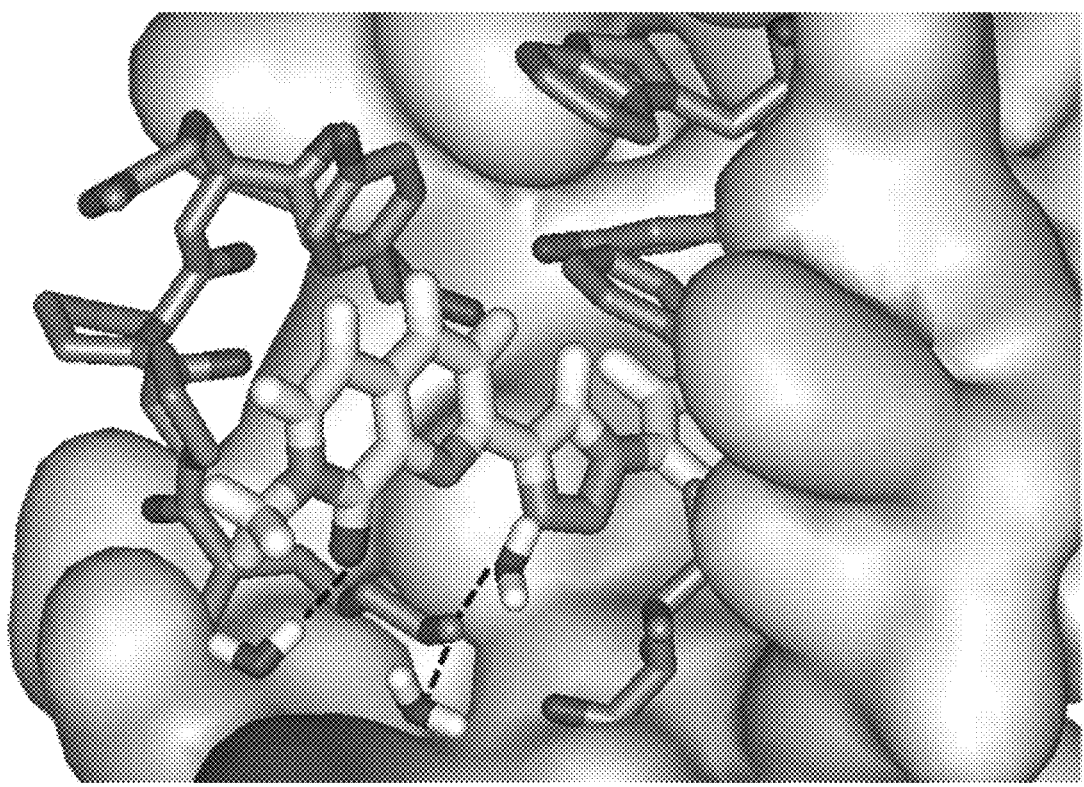
FIG. 6 illustrates an image derived from a Monte Carlo simulation of 3a (carbon atoms in light gray) showing two water molecules hydrogen-bonded with Lys32 and one with the carbonyl group of 3a. Lys32 is participating in a total of six hydrogen bonds.

Though the FEP results turned out to be qualitatively correct, the confidence level is not yet at the point where one rejects pursuit of analogs as tempting as 3 and 4. Traditional scoring functions used in docking calculations typically count well-formed protein-ligand hydrogen bonds like the present cases as contributing 1 kcal/mol (a factor of 5) to binding affinity. Thus, the outcome is context dependent, being sensitive to the complex balance of protein-ligand, protein-water, and ligand-water interactions. In viewing complexes for 1a and 3a from the Monte Carlo simulations, one might expect one less hydrogen bond between water molecules and Lys32 for 3a. However, for both 1a and 3a, there are consistently two water molecules hydrogen-bonded to Lys32, and for 3a, there is an additional hydrogen bond with the naphthyridinone carbonyl group (FIG. 6). For the unbound 3a, there is also just one water molecule hydrogen-bonded to the carbonyl group. Thus, the origins of the presumably greater dehydration penalty upon binding 3a rather than 1a, which offsets the added protein-ligand hydrogen bond with 3a, are subtle and likely dominated by entropy effects.

TABLE 1

Experimental Inhibition Constants K$_i$, Binding Constants K$_d$ (µM), and Aqueous Solubility S (µg/mL)

| Cmpd | R | K$_i$ | K$_d$ | S |
|---|---|---|---|---|
| 1a | H | 0.23 | 0.26 | 2.2 |
| 1b | HOCH$_2$CH$_2$O | 0.53 | ND | 2.6 |
| 1c[a] | H$_2$NCH$_2$CH$_2$O | 0.26 | ND | 3.7 |
| 1d[a] | H$_2$N(CH$_2$CH$_2$O)$_2$ | 0.36 | 0.35 | 13.9 |
| 1e[b] | 4-Mr(CH$_2$CH$_2$O)$_2$ | 0.16 | 0.21 | 48.5 |

TABLE 1-continued

Experimental Inhibition Constants $K_i$, Binding Constants $K_d$ (μM), and Aqueous Solubility S (μg/mL)

| Cmpd | R | $K_i$ | $K_d$ | S |
|---|---|---|---|---|
| 1f | HOOCCH$_2$O | 0.20 | ND | 365 |
| 2a[a] | H$_2$N(CH$_2$CH$_2$O)$_2$ | 0.144 | 0.16 | 9.1 |
| 2b | 4-Mr(CH$_2$CH$_2$O)$_2$ | 0.074 | 0.15 | 27.2 |
| 2c | HOOCCH$_2$O | 0.048 | ND | 37.0 |
| 2d | HOOC(CH$_2$)$_3$O | 0.039 | 0.063 | 19.2 |
| 3a | H$_3$C | 0.363 | 0.213 | ND |
| 4a | H$_3$C | 0.075 | 0.111 | ND |
| 4b | HOOCCH$_2$ | 0.090 | 0.094 | 288 |
| ISO-1 | | 30.1 | 23.1 | ND |

[a]TFA salt.
[b]Mr = morpholinyl.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in pharmaceutical science and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, in certain other embodiments ±5%, in other embodiments ±1%, and in yet other embodiments ±0.1% from the specified value, as such variations are appropriate to perform the disclosed methods.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "ED$_{50}$" or "ED50" refers to the effective dose of a formulation that produces about 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition.

As used herein, a "patient" or "subject" may be a human or non-human mammal or a bird. Non-human mammals include, for example, livestock and pets, such as ovine, bovine, porcine, canine, feline and murine mammals. In certain other embodiments, the subject is human.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, pulmonary and topical administration.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

The term "solvate," as used herein, refers to a compound formed by solvation, which is a process of attraction and association of molecules of a solvent with molecules or ions of a solute. As molecules or ions of a solute dissolve in a solvent, they spread out and become surrounded by solvent molecules.

The term "treat," "treating" or "treatment," as used herein, means reducing the frequency or severity with which symptoms of a disease or condition are experienced by a subject by virtue of administering an agent or compound to the subject.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "cycloalkyl," by itself or as part of another substituent means, unless otherwise stated, a cyclic chain hydrocarbon having the number of carbon atoms designated (i.e., C3-C6 means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies.

As used herein, the term "substituted alkyl", "substituted cycloalkyl", "substituted alkenyl", "substituted alkynyl", "substituted alkylene", "substituted alkenylene", "substituted alkynylene", "substituted heteroalkyl", "substituted heteroalkenyl", "substituted heteroalkynyl", "substituted aryl", "substituted heteroaryl" or "substituted heterocyclyl" means alkyl, cycloalkyl, alkenyl, alkynyl, alkylene, alkenylene, alkynylene, heteroalkyl, heteroalkenyl, heteroalkynyl, aryl, heteroaryl, or heterocyclyl as defined above, substituted by one, two or three substituents selected from the group consisting of $C_1$-$C_{10}$ alkyl, halogen, perhaloakyl, =O, —OH, alkoxy, tetrahydro-2-H-pyranyl, —$NH_2$, —$N(CH_3)_2$, phenyl, benzyl, (1-methyl-imidazol-2-yl), pyridin-2-yl, pyridin-3-yl, pyridin-4-yl, —C(=O)OH, trifluoromethyl, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" or "heterocycloalkyl" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain other embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3 dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group. Non-limiting examples of "substituted" groups include $C_1$-$C_{10}$ alkyl, halogen, perhaloakyl, =O, —OH, alkoxy, —$NH_2$, —N($CH_3$)$_2$, phenyl, benzyl, (1-methyl-imidazol-2-yl), pyridin-2-yl, pyridin-3-yl, pyridin-4-yl, —C(=O)OH, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain other embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred. The term "substituted heterocycle" and "substituted heteroaryl" as used herein refers to a heterocycle or heteroaryl group having one or more substituents including halogen, CN, OH, $NO_2$, amino, alkyl, cycloalkyl, carboxyalkyl (C(O)Oalkyl), trifluoroalkyl such as $CF_3$, aryloxy, alkoxy, aryl, or heteroaryl. A substituted heterocycle or heteroaryl group may have 1, 2, 3, or 4 substituents.

The following abbreviations are used herein: DFT, density functional theory; FEP, free-energy perturbation; DCM, dichloromethane; DMF, dimethylformamide; MIF, macrophage migration inhibitory factor; TBAF, tetrabutylammonium fluoride Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

The invention includes a compound of formula (I), or a salt, solvate, enantiomer, diastereoisomer, geometric isomer, or tautomer thereof:

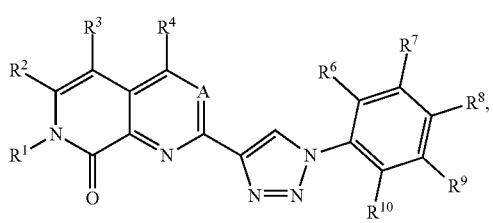

(I)

wherein:
A is $CR^5$ or N;
$R^1$ is selected from the group consisting of H, $C_1$-$C_6$ alkyl, and $C_1$-$C_6$ heteroalkyl, wherein the alkyl or heteroalkyl group is optionally substituted with at least one selected from the group consisting of —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR, $R^2$ and $R^3$ are independently selected from the group consisting of H, halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, ($C_3$-$C_7$ cycloalkyl)-$C_1$-$C_4$ alkylene, ($C_6$-$C_{10}$ aryl)-$C_1$-$C_4$ alkylene, (5-10 membered heteroaryl)-$C_1$-$C_4$ alkylene, (4-10 membered heterocyclyl)-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR;

or one of $R^2$ and $R^3$ is -L-$R^{11}$, wherein:
L is selected from the group consisting of a bond, —O—, —N(R)—, $C_1$-$C_4$ alkylene, —C(=O)—, —N(R)C(=O)—, and —C(=O)N(R)—; and
$R^{11}$ is optionally substituted phenyl, pyridinyl, or pyrimidinyl;

$R^4$, $R^5$, $R^6$, and $R^m$ are each independently selected from the group consisting of H, halogen, $C_1$-$C_6$ alkyl, and $C_1$-$C_6$haloalkyl;

$R^7$, $R^8$, and $R^9$ are independently selected from the group consisting of H, halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, ($C_3$-$C_7$ cycloalkyl)-$C_1$-$C_4$ alkylene, ($C_6$-$C_{10}$ aryl)-$C_1$-$C_4$ alkylene, (5-10 membered heteroaryl)-$C_1$-$C_4$ alkylene, (4-10 membered heterocyclyl)-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR;

each occurrence of R is independently selected from the group consisting of H, $C_1$-$C_6$ alkyl, $C_2$-$C_6$ alkenyl, $C_2$-$C_6$ alkynyl, $C_3$-$C_8$ cycloalkyl, or $C_3$-$C_8$ heterocyclyl, or the two R bound to the same N optionally form a $C_3$-$C_8$ heterocyclyl group;

each occurrence of R' is independently selected from the group consisting of $C_1$-$C_6$ alkyl, $C_2$-$C_6$ alkenyl, $C_2$-$C_6$ alkynyl, $C_3$-$C_8$ cycloalkyl, or $C_3$-$C_8$ heterocyclyl;

each alkyl, alkenyl, alkynyl, cycloalkyl, or heterocyclyl group is optionally substituted with at least one substituent selected from the group consisting of halogen, $C_6$-$C_{10}$ aryl, 5-10 membered heteroaryl, 4-10 membered heterocyclyl, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR;

each phenyl or heteroaryl group is optionally substituted with at least one substituent selected from the group consisting of halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, $C_3$-$C_7$ cycloalkyl-$C_1$-$C_4$ alkylene, $C_6$-$C_{10}$ aryl-$C_1$-$C_4$ alkylene, 5-10 membered heteroaryl-$C_1$-$C_4$ alkylene, 4-10 membered heterocyclyl-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR.

In certain embodiments, the compound is a compound of formula (Ia):

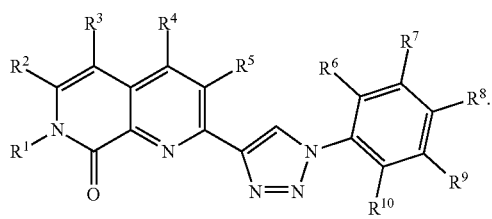

(Ia)

In certain embodiments, the compound is a compound of formula (Ib):

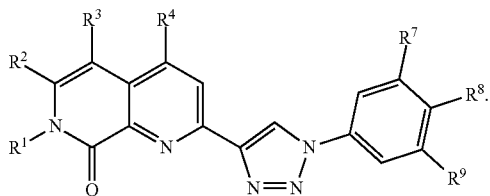

In certain embodiments, the compound is a compound of formula (Ic):

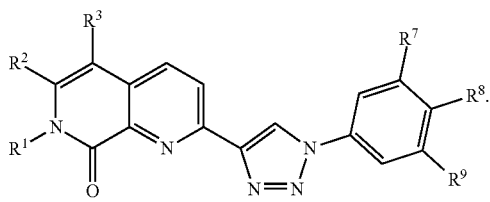

In certain embodiments, the compound is a compound of formula (Id):

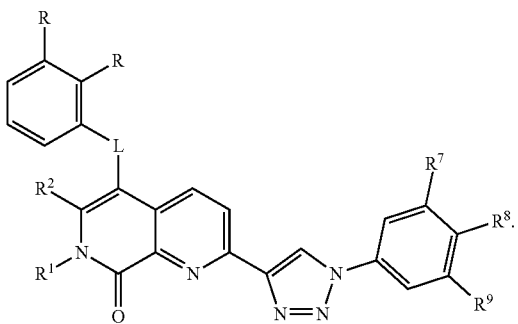

In certain embodiments, the compound is selected from the group consisting of 3a, 4a, and 4b. In other embodiments, the compound is not 3a. In yet other embodiments, the compound is not 4a. In yet other embodiments, the compound is not 4b.

In certain embodiments, $R^1$ is H. In other embodiments, $R^1$ is —$CH_3$. In yet other embodiments, $R^1$ is —$CH_2CH_2OH$. In yet other embodiments, $R^1$ is —$CH_2CH_2NH_2$. In yet other embodiments, $R^1$ is —$CH_2CH_2OCH_2CH_2OH$. In yet other embodiments, $R^1$ is —$CH_2CH_2OCH_2CH_2NH_2$. In yet other embodiments, $R^1$ is —$CH_2CH_2OCH_2CH_2$-4-morpholinyl. In yet other embodiments, $R^1$ is —$CH_2COOH$. In yet other embodiments, $R^1$ is —$CH_2CH_2COOH$. In yet other embodiments, $R^1$ is —$CH_2CH_2CH_2COOH$.

In certain embodiments, $R^1$ is not H. In other embodiments, $R^1$ is not —$CH_3$. In yet other embodiments, $R^1$ is not —$CH_2CH_2OH$. In yet other embodiments, $R^1$ is not —$CH_2CH_2NH_2$. In yet other embodiments, $R^1$ is not —$CH_2CH_2OCH_2CH_2OH$. In yet other embodiments, $R^1$ is not —$CH_2CH_2OCH_2CH_2NH_2$. In yet other embodiments, $R^1$ is not —$CH_2CH_2OCH_2CH_2$-4-morpholinyl. In yet other embodiments, $R^1$ is not —$CH_2COOH$. In yet other embodiments, $R^1$ is not —$CH_2CH_2COOH$. In yet other embodiments, $R^1$ is not —$CH_2CH_2CH_2COOH$.

In certain embodiments, $R^2$ is H or —OR.

In certain embodiments, $R^3$ is selected from the group consisting of H, $C_6$-$C_{10}$ aryl, and —OR. In other embodiments, $R^3$ is H, unsubstituted phenyl, phenyl substituted with 1 substituent selected from the group consisting of $C_1$-$C_6$ alkyl, halogen, $C_1$-$C_6$ alkoxy, and —OR″, wherein R″ is unsubstituted phenyl or phenyl substituted with 1 group independently selected from the group consisting of —OR and —C(=O)OR. In yet other embodiments, $R^3$ is H, 4-methoxyphenyl, 4-(2-methoxy(ethoxy))phenyl, 4-carboxyphenyl, or phenoxy.

In certain embodiments, one of $R^2$ and $R^3$ is -L-$R^{11}$. In other embodiments, L is O or NH.

In certain embodiments, $R^2$ and an optional substituent in $R^{11}$ are independently selected from the group consisting of H, $C_1$-$C_6$ alkoxy, $C_1$-$C_6$ alkoxy-$C_1$-$C_6$ alkyl, carboxy, carboxy-$C_1$-$C_6$ alkyl, amino-$C_1$-$C_6$ alkyl, $C_1$-$C_6$ alkylamino-$C_1$-$C_6$ alkyl, di($C_1$-$C_6$ alkyl)amino-$C_1$-$C_6$ alkyl, amino-$C_1$-$C_6$ alkoxy-$C_1$-$C_6$ alkyl, $C_1$-$C_6$ alkylamino-$C_1$-$C_6$ alkoxy-$C_1$-$C_6$ alkyl, di($C_1$-$C_6$ alkyl)amino-$C_1$-$C_6$ alkoxy-$C_1$-$C_6$ alkyl, 4-10 membered heterocyclyl-$C_1$-$C_6$ alkyl, 4-10 membered heterocyclyl-$C_1$-$C_6$ alkoxy-$C_1$-$C_6$ alkyl, $C_1$-$C_6$ alkoxy-$C_1$-$C_6$ alkoxy, amino-$C_1$-$C_6$ alkoxy, $C_1$-$C_6$ alkylamino-$C_1$-$C_6$ alkoxy, di($C_1$-$C_6$ alkyl)amino-$C_1$-$C_6$ alkoxy, amino-$C_1$-$C_6$ alkoxy-$C_1$-$C_6$ alkoxy, $C_1$-$C_6$ alkylamino-$C_1$-$C_6$ alkoxy-$C_1$-$C_6$ alkoxy, di($C_1$-$C_6$ alkyl)amino-$C_1$-$C_6$ alkoxy-$C_1$-$C_6$ alkoxy, 4-10 membered heterocyclyl-$C_1$-$C_6$ alkoxy, 4-10 membered heterocyclyl-$C_1$-$C_6$ alkoxy, carboxy-$C_1$-$C_6$ alkoxy, carboxy-$C_1$-$C_6$ alkyl-$C_1$-$C_6$ alkoxy, and carboxy-$C_1$-$C_6$ alkoxy-$C_1$-$C_6$ alkoxy. In other embodiments, $R^3$ is H, —OR, or $C_1$-$C_6$ alkyl substituted with one or more substituents selected from —OR, —C(=O)OR, and —NRR.

In certain embodiments, $R^4$ is H or $C_1$-$C_6$ alkyl. In other embodiments, $R^4$ is selected from the group consisting of H, F, methyl, and ethyl.

In certain embodiments, $R^5$ is H or $C_1$-$C_6$ alkyl. In other embodiments, $R^5$ is selected from the group consisting of H, F, methyl, and ethyl.

In certain embodiments, $R^6$ is H. In other embodiments, $R^7$ is halogen, $C_1$-$C_6$ alkyl, or —OR. In yet other embodiments, $R^8$ is —OH, halogen, —CN, —OR, —NRR, or —C(=O)NRR. In yet other embodiments, $R^9$ is H or halogen. In yet other embodiments, $R^{10}$ is H. In yet other embodiments, $R^6$, $R^7$, $R^9$, and $R^{10}$ are each independently selected from the group consisting of H and F. In yet other embodiments, $R^8$ is selected from the group consisting of H, F, Cl, and —OH.

The compounds described herein can form salts with acids and/or bases, and such salts are included in the present invention. In certain other embodiments, the salts are pharmaceutically acceptable salts. The term "salts" embraces addition salts of free acids and/or bases that are useful within the methods of the invention. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate).

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, ammonium, N,N'-dibenzylethylene-diamine, chloroprocaine, choline, diethanolamine, ethylenediamine, meglumine (N-methylglucamine) and procaine.

All of these salts may be prepared from the corresponding compound by reacting, for example, the appropriate acid or base with the compound. Salts may be comprised of a fraction of less than one, one, or more than one molar equivalent of acid or base with respect to any compound of the invention.

In certain other embodiments, the at least one compound of the invention is a component of a pharmaceutical composition further including at least one pharmaceutically acceptable carrier.

The compounds of the invention may possess one or more stereocenters, and each stereocenter may exist independently in either the (R) or (S) configuration. In certain other embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain other embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain other embodiments, the compounds described herein exist in solvated forms with pharmaceutically acceptable solvents such as water, and ethanol. In other embodiments, the compounds described herein exist in unsolvated form.

In certain other embodiments, the compounds of the invention exist as tautomers. All tautomers are included within the scope of the compounds recited herein.

In certain other embodiments, compounds described herein are prepared as prodrugs. A "prodrug" is an agent converted into the parent drug in vivo. In certain other embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain other embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain other embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain other embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain other embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and in the art. General methods for the preparation of compound as described herein are modified by the use of appropriate reagents and conditions, for the introduction of the various moieties found in the formula as provided herein.

Methods

The invention provides a method of inhibiting macrophage migration inhibitory factor (MIF) activity in a subject. The invention further provides a method of treating a disease or condition in which inhibition of macrophage migration inhibitory factor (MIF) activity in a subject is therapeutically beneficial. The invention further provides a method of treating an inflammatory disease or condition in a subject. The invention further provides a method of treating an autoimmune disease in a subject. The invention further provides a method of treating cancer in a subject. The invention further provides a method of treating a disease or condition associated with high MIF expression in a subject. The invention further provides a method of treating anemia of chronic disease in a subject. In certain embodiments, the method comprises administering to the subject an effective amount of a compound of the invention, or a pharmaceutically acceptable salt or solvate thereof.

In certain embodiments, the inflammatory disease or condition is selected from the group consisting of proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type 1 diabetes, type 2 diabetes, Berger's disease, Retier's syndrome, and Hodgkin's disease.

In certain embodiments, the autoimmune disease is selected from the group consisting of multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome, and autoimmune inflammatory eye disease.

In certain embodiments, the cancer is a solid tumor or a hematological cancer.

In certain embodiments, the cancer is selected from the group consisting of prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin's lymphoma (including relapsed non-Hodgkin's lymphoma, refractory non-Hodg- kin's lymphoma and recurrent follicular non-Hodgkin's lymphoma), Hodgkin's lymphoma, and multiple myeloma.

In certain embodiments, the disease or condition associated with high MIF expression is selected from the group consisting of protozoal infection, fungal infection, bacterial infection, viral infection, anemia of chronic disease, asthma, and autism spectrum disorder (ASD).

Combination Therapies

The compounds of the present invention are intended to be useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes.

For treating autoimmune or inflammatory conditions, the compound of the invention can be administered in combination with an immune suppressant such as fluocinolone acetonide (RETISERT®), rimexolone (AL-2178, Vexol, Alcon), or cyclosporine (RESTASIS®).

For treating autoimmune or inflammatory conditions, the compound of the invention can be administered in combination with one or more additional agents selected from DEHYDREX® (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, IDESTRIN® (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (EMBREL®), hydroxychloroquine, NGX267 (TorreyPines Therapeutics), or thalidomide.

For the prophylaxis or treatment of anemia of chronic disease comprising, the compounds of the invention can be used in combination with one or more other agents that stimulate erythropoiesis such as erythropoietin ("EPO"), iron, folate, vitamin B12, blood, blood substitute, and plasma or serum that contains a composition with the activity of blood. In other embodiments, the MIF antagonist can be administered in combination with a tumor necrosis factor-α (TNFα) antagonist or an interferon (IFN) antagonist (e.g., an IFNγ antagonist) to a subject. Examples of TNFα and IFNγ antagonists include, without limitation, anti-TNF, soluble TNF receptor, anti-IFNγ, soluble IFNγ receptor, p38 MAPK inhibitors, and JAK-STAT inhibitors.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle.

In certain other embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating or preventing diseases and disorders discussed herein) in the composition. In yet other embodiments, the compound of the invention is the only biologically active agent (i.e., capable of treating or preventing diseases and disorders discussed herein) in therapeutically effective amounts in the composition.

In certain other embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 300 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments thereinbetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain other embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include intravitreal, oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravitreal, intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intravitreal, intraperitoneal, intramuscular, intrasternal injection, and kidney dialytic infusion techniques.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient that is solid at ordinary room temperature (i.e., about 20° C.) and liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Controlled Release Formulations and Drug Delivery Systems

In certain other embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form. In certain embodiments, the compounds of the invention can be formulated for sustained release over a period of 3-12 months.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain other embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

NMR spectra were recorded on Agilent DD2 600 (600 MHz), DD2 500 (500 MHz) and DD2 400 (400 MHz) instruments. Column chromatography was carried out using CombiFlash over redisep column cartridges employing Merck silica gel (Kieselgel 60, 63-200 µm). Pre-coated silica gel plates F-254 were used for thin-layer analytical chromatography. HRMS (ESI-TOF) analyses were performed on Waters Xevo QTOF equipped with Z-spray electrospray ionization source. The purity (≥95%) of all final synthesized compounds was determined by reverse phase HPLC, using a Waters 2487 dual λ absorbance detector with a Waters 1525 binary pump and a Phenomenex Luna 5µ C18(2) 250×4.6 mm column. Samples were run at 1 mL/min using gradient mixtures of 5-100% of water with 0.1% trifluoroacetic acid (TFA) (A) and 10:1 acetonitrile:water with 0.1% TFA (B) for 22 min followed by 3 min at 100% B.

Example 1: Synthesis of Compounds 3 and 4

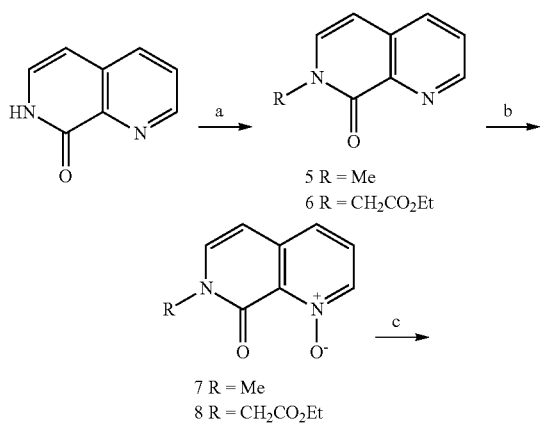

Scheme 2. Synthesis of compounds 3 and 4.

5 R = Me
6 R = CH₂CO₂Et

7 R = Me
8 R = CH₂CO₂Et

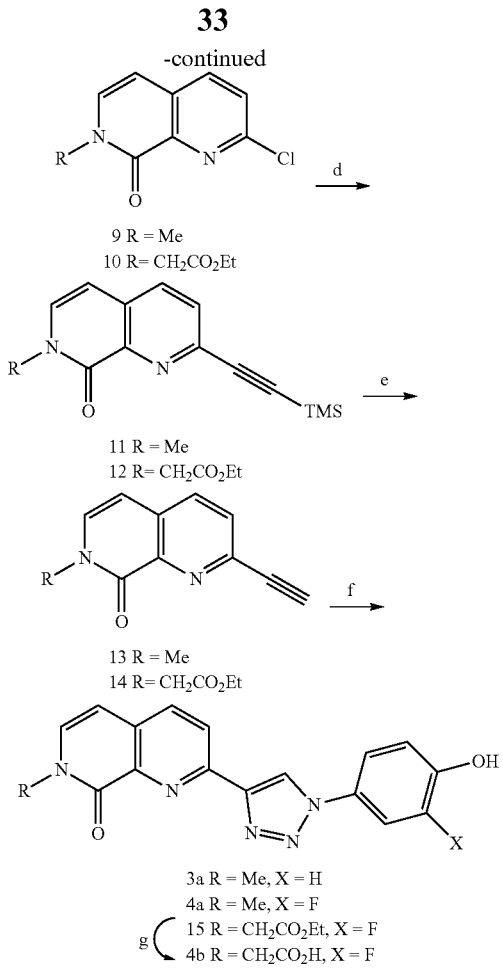

Reagents and conditions: (a) MeI or ethyl bromoacetate, K₂CO₃, DMF, 15 h, r.t.; (b) mCPBA, DCM, 15 h, r.t.; (c) oxalyl chloride, DMF, 5 h, 0° C. to r.t.; (d) TMS-acetylene, Pd(PPH₃)₂Cl₂, CuI, TEA, DMF, 15 h, 60° C.; (e) TBAF, DMF, 0.5 h, r.t. (f) NaN₃, NaAscO, CuI, 4-iodophenol or 2-fluoro-4-iodophenol, (1R,2R)-N¹,N²-dimethylcyclohexane-1,2-diamine, DMSO, H₂O, 15 h, 70° C., (g) NaOH, dioxane, 15 h, r.t.

General Procedure a:

$K_2CO_3$ (2.0 eq.) was added to a solution of 1,7-naphthyridin-8(7H)-one (1.0 eq.) in anhydrous DMF (0.1 M), followed by the addition of iodomethane or ethyl bromoacetate (4.0 eq.). The reaction was stirred at room temperature for 15 h. After evaporation of DMF, the desired intermediate was purified by flash chromatography (DCM/MeOH).

7-methyl-1,7-naphthyridin-8(7H)-one (5)

Yield 88%. ¹H NMR (400 MHz, Chloroform-d) δ 8.85 (dd, J=4.3, 1.7 Hz, 1H), 7.89 (dd, J=8.1, 1.7 Hz, 1H), 7.54 (dd, J=8.1, 4.4 Hz, 1H), 7.23 (d, J=7.3 Hz, 1H), 6.43 (d, J=7.3 Hz, 1H), 3.66 (s, 3H). MS (ESI) m/z 161.1 [M+H].

Ethyl 2-(8-oxo-1,7-naphthyridin-7(8H)-yl)acetate (6)

Yield 88%. ¹H NMR (400 MHz, Chloroform-d) δ 8.88 (dd, J=4.4, 1.6 Hz, 1H), 7.88 (dd, J=8.1, 1.7 Hz, 1H), 7.55 (dd, J=8.1, 4.4 Hz, 1H), 7.10 (d, J=7.3 Hz, 1H), 6.47 (d, J=7.3 Hz, 1H), 4.80 (s, 2H), 4.25 (q, J=7.1 Hz, 2H), 1.29 (t, J=7.1 Hz, 3H). MS (ESI) m/z 233.1 [M+H].

General Procedure b:

mCPBA (1.5 eq.) was added in one portion to a solution of the corresponding substituted naphthyridinone (1.0 eq.) in anhydrous DCM (0.1 M) and the reaction stirred for 15 h at room temperature. DCM was evaporated and the intermediate purified by flash chromatography (DCM/MeOH).

7-methyl-8-oxo-7,8-dihydro-1,7-naphthyridine 1-oxide (7)

Yield 70%. ¹H NMR (400 MHz, Chloroform-d) δ 8.28 (dd, J=6.3, 1.1 Hz, 1H), 7.30 (dd, J=8.2, 6.3 Hz, 1H), 7.22 (dd, J=8.1, 1.1 Hz, 1H), 7.18 (d, J=7.3 Hz, 1H), 6.31 (d, J=7.3 Hz, 1H), 3.56 (s, 3H). MS (ESI) m/z 177.1 [M+H].

7-(2-ethoxy-2-oxoethyl)-8-oxo-7,8-dihydro-1,7-naphthyridine 1-oxide (8)

Yield 81%. ¹H NMR (400 MHz, Chloroform-d) δ 8.30 (dd, J=6.4, 1.1 Hz, 1H), 7.34 (dd, J=8.1, 6.4 Hz, 1H), 7.23 (dd, J=8.1, 1.1 Hz, 1H), 7.11 (d, J=7.4 Hz, 1H), 6.36 (d, J=7.3 Hz, 1H), 4.64 (s, 2H), 4.24 (q, J=7.1 Hz, 2H), 1.29 (t, J=7.1 Hz, 3H). MS (ESI) m/z 249.1 [M+H].

General Procedure c:

Oxalyl chloride (2.0 eq.) was added dropwise to a solution of the corresponding naphthyridinone N-oxide (1.0 eq.) in anhydrous DMF (0.1 M) at 0° C. The mixture was allowed to warm to room temperature and stirred for 5 h. After solvent evaporation, the intermediate was purified by flash chromatography (DCM/MeOH).

2-chloro-7-methyl-1,7-naphthyridin-8(7H)-one (9)

Yield 57%. ¹H NMR (400 MHz, Chloroform-d) δ 7.83 (d, J=8.4 Hz, 1H), 7.53 (d, J=8.4 Hz, 1H), 7.20 (d, J=7.3 Hz, 1H), 6.42 (d, J=7.3 Hz, 1H), 3.66 (s, 3H). MS (ESI) m/z 195.0 [M+H].

Ethyl 2-(2-chloro-8-oxo-1,7-naphthyridin-7(8H)-yl)acetate (10)

Yield 68%. ¹H NMR (400 MHz, Chloroform-d) δ 7.84 (d, J=8.4 Hz, 1H), 7.55 (d, J=8.5 Hz, 1H), 7.14 (d, J=7.3 Hz, 1H), 6.46 (d, J=7.3 Hz, 1H), 4.77 (s, 2H), 4.24 (q, J=7.1 Hz, 2H), 1.29 (t, J=7.1 Hz, 3H). MS (ESI) m/z 267.0 [M+H].

General Procedure d:

Corresponding chloro-naphthyridinone (1.0 eq.) was dissolved in anhydrous DMF (0.57 M, degassed by purging with N₂ while sonicating for 15 min) in a pressure vial. TEA (4.0 eq., degassed separately) was added, followed by Pd(PPh₃)₂Cl₂ (0.1 eq.) and CuI (0.1 eq.). Finally, TMS-acetylene (2.0 eq.) was added, the vial sealed, and the mixture stirred 15 h at 60° C. The DMF was evaporated and the intermediate purified by flash chromatography (DCM/MeOH).

7-methyl-2-((trimethylsilyl)ethynyl)-1,7-naphthyridin-8(7H)-one (11)

Yield 39%. ¹H NMR (400 MHz, Methanol-d⁴) δ 8.06 (d, J=8.3 Hz, 1H), 7.73 (d, J=8.3 Hz, 1H), 7.49 (d, J=7.3 Hz, 1H), 6.64 (d, J=7.3 Hz, 1H), 3.64 (s, 3H), 0.27 (s, 9H). MS (ESI) m/z 257.1 [M+H].

Ethyl 2-(8-oxo-2-((trimethylsilyl)ethynyl)-1,7-naphthyridin-7(8H)-yl)acetate (12)

Yield 60%. ¹H NMR (400 MHz, Chloroform-d) δ 7.78 (d, J=8.3 Hz, 1H), 7.61 (d, J=8.3 Hz, 1H), 7.10 (d, J=7.3 Hz, 1H), 6.40 (d, J=7.4 Hz, 1H), 4.74 (s, 2H), 4.20 (q, J=7.1 Hz, 2H), 1.25 (t, J=7.1 Hz, 3H), 0.24 (s, 9H). MS (ESI) m/z 329.1 [M+H].

General Procedure e:

TBAF (1.25 eq., 1.0 M in THF) was added dropwise to the TMS-protected alkynyl naphthyridinone (1.0 eq.) dissolved in anhydrous DMF (0.1 M) and the reaction stirred 30 min at room temperature. The DMF was evaporated and the intermediate purified by flash chromatography (DCM/MeOH).

2-ethynyl-7-methyl-1,7-naphthyridin-8(7H)-one (13)

Yield 47%. $^1$H NMR (400 MHz, Methanol-d$^4$) δ 8.10 (d, J=8.3 Hz, 1H), 7.78 (d, J=8.3 Hz, 1H), 7.51 (d, J=7.3 Hz, 1H), 6.67 (d, J=7.3 Hz, 1H), 3.87 (s, 1H), 3.65 (s, 3H). MS (ESI) m/z 185.1 [M+H].

Ethyl 2-(2-ethynyl-8-oxo-1,7-naphthyridin-7(8H)-yl)acetate (14)

Yield 23%. $^1$H NMR (400 MHz, Chloroform-d) δ 7.79 (d, J=8.3 Hz, 1H), 7.59 (d, J=8.2 Hz, 1H), 7.15 (d, J=7.3 Hz, 1H), 6.40 (d, J=7.4 Hz, 1H), 4.74 (s, 2H), 4.16 (q, J=7.1 Hz, 2H), 3.19 (s, 1H), 1.21 (t, J=7.1 Hz, 3H). MS (ESI) m/z 257.1 [M+H].

General Procedure f:

Trans-N,N'-dimethyl-1,2-cyclohexanediamine (0.4 eq.), 4-iodophenol or 2-fluoro-4-iodophenol (2.0 eq.), NaN$_3$ (2.0 eq.), sodium ascorbate (0.8 eq.), and CuI (0.4 eq.) were dissolved in DMSO (0.31 M, degassed). The mixture was stirred at 70° C. in a sealed pressure vial for 2 h. Next, the corresponding alkynyl naphthyridinone (1.0 eq.) was added, transferred with additional DMSO (0.46 M). Finally, H$_2$O was added (0.92 M), and the reaction stirred overnight at 70° C. The reaction mixture was concentrated in vacuo and purified by flash chromatography (DCM/MeOH) to yield the desired final products.

2-(1-(4-hydroxyphenyl)-1H-1,2,3-triazol-4-yl)-7-methyl-1,7-naphthyridin-8(7H)-one (3a)

Using 4-iodophenol (0.071 g, 0.32 mmol). Yield 23%. $^1$H NMR (400 MHz, DMSO-d$^6$) δ 10.03 (bs, 1H), 9.23 (s, 1H), 8.39 (s, 1H), 8.26 (d, J=8.4 Hz, 1H), 7.82 (d, J=8.4 Hz, 2H), 7.60 (d, J=7.2 Hz, 1H), 6.97 (d, J=8.4 Hz, 2H), 6.67 (s, 1H), 3.57 (s, 3H). $^{13}$C NMR (151 MHz, DMSO-d$^6$) δ 160.1, 158.0, 148.9, 147.6, 140.9, 135.9, 134.8, 132.8, 128.6, 123.1, 122.2, 121.5, 116.0, 102.9, 36.9. HRMS (ESI): calc. for [M+H]$^+$ C$_{17}$H$_{14}$N$_5$O$_2$ 320.1142, found 320.1147.

2-(1-(3-fluoro-4-hydroxyphenyl)-1H-1,2,3-triazol-4-yl)-7-methyl-1,7-naphthyridin-8(7H)-one (4a)

Using 2-fluoro-4-iodophenol (0.085 g, 0.36 mmol). Yield 20%. $^1$H NMR (500 MHz, DMSO-d$^6$) δ 10.50 (bs, 1H), 9.27 (s, 1H), 8.38 (d, J=8.4 Hz, 1H), 8.24 (d, J=8.4 Hz, 1H), 7.97 (dd, J=11.9, 2.6 Hz, 1H), 7.73 (ddd, J=8.7, 2.6, 1.2 Hz, 1H), 7.60 (d, J=7.2 Hz, 1H), 7.14 (t, J=9.0 Hz, 1H), 6.65 (d, J=7.2 Hz, 1H), 3.56 (s, 3H). $^{13}$C NMR (126 MHz, DMSO-d$^6$) δ 160.1, 150.7 (d, J=242.6 Hz), 148.8, 147.7, 145.7 (d, J=12.0 Hz), 140.9, 136.0, 134.9, 132.9, 128.2 (d, J=9.1 Hz), 123.1, 121.7, 118.2 (d, J=3.9 Hz), 117.0 (d, J=3.3 Hz), 109.5 (d, J=23.3 Hz), 102.9, 37.0. HRMS (ESI): calc. for [M+H]$^+$ C$_{17}$H$_{13}$FN$_5$O$_2$ 338.1048, found 338.1053.

Synthesis of Final Compound 4b:

Compound 4b has been obtained by hydrolysis of the corresponding ethyl ester precursor (method g). 15 (1.0 eq.) was dissolved in 1,4-dioxane (0.013 M), and 2.0 M NaOH (25 eq.) was added. After the reaction was stirred 15 h at room temperature, dioxane was evaporated and the remaining mixture diluted in H$_2$O. The pH was adjusted to 3 using 1 N HCl, and the solution extracted three times with EtOAc. The combined organic layers were dried over anhydrous Na$_2$SO$_4$ and concentrated. Purification by flash chromatography (DCM/MeOH) afforded the final product.

Ethyl 2-(2-(1-(3-fluoro-4-hydroxyphenyl)-1H-1,2,3-triazol-4-yl)-8-oxo-1,7-naphthyridin-7(8H)-yl)acetate (15)

According to general procedure f using 2-fluoro-4-iodophenol. Yield 60%. $^1$H NMR (400 MHz, DMSO-d$^6$) δ 10.59 (bs, 1H), 9.28 (s, 1H), 8.43 (s, 1H), 8.29 (d, J=8.3 Hz, 1H), 7.96 (d, J=11.8 Hz, 1H), 7.72 (d, J=8.7 Hz, 1H), 7.60 (d, J=7.3 Hz, 1H), 7.15 (t, J=8.7 Hz, 1H), 6.78-6.68 (m, 1H), 4.83 (s, 2H), 4.17 (q, J=7.0 Hz, 2H), 1.23 (t, J=7.0 Hz, 3H). MS (ESI) m/z 410.1 [M+H].

2-(2-(1-(3-fluoro-4-hydroxyphenyl)-1H-1,2,3-triazol-4-yl)-8-oxo-1,7-naphthyridin-7(8H)-yl)acetic acid (4b)

Yield quantitative. $^1$H NMR (600 MHz, DMSO-d$^6$) δ 10.68 (bs, 1H), 9.27 (s, 1H), 8.38 (d, J=8.4 Hz, 1H), 8.25 (d, J=8.4 Hz, 1H), 7.96 (dd, J=11.9, 2.6 Hz, 1H), 7.72 (ddd, J=8.6, 2.7, 1.1 Hz, 1H), 7.49 (d, J=7.2 Hz, 1H), 7.17 (t, J=9.0 Hz, 1H), 6.62 (d, J=7.2 Hz, 1H), 4.51 (s, 2H). $^{13}$C NMR (151 MHz, DMSO-d$^6$) δ 169.6, 160.2, 151.2 (d, J=242.6 Hz), 148.9, 148.1, 146.1 (d, J=11.5 Hz), 141.5, 136.3, 135.8, 133.4, 128.6 (d, J=8.4 Hz), 123.5, 122.1, 118.6 (d, J=4.0 Hz), 117.4 (d, J=3.4 Hz), 109.9 (d, J=23.4 Hz), 102.6, 52.1. HRMS (ESI): calc. for [M+H]$^+$ C$_{18}$H$_{13}$FN$_5$O$_4$ 382.0946, found 382.0952.

Example 2: Protein Crystallography

Crystallization of MIF in Complex with 3a, 4a and 4b:

Recombinant expression and purification of MIF was performed as reported previously (Dziedzic, et al., 2015, J. Am. Chem. Soc. 137:2996-3003). Co-crystallization of MIF in complex with 3a, 4a and 4b was performed by sitting drop vapor diffusion at 20° C. 2 μL of MIF (20 mg/mL) in a solution composed of 50 mM TRIS pH 7.4 and 150 mM NaCl was added to 2 μL of reservoir solution containing a 2 mM suspension of the respective ligand taken from a 50 mM DMSO stock solution. For 3a, a reservoir of 2.6 M (NH$_4$)$_2$SO$_4$, 0.1 M Tris pH 7.0 and 3% isopropanol was used. 4a and 4b crystallized in a reservoir solution composed of 2.1 M (NH$_4$)$_2$SO$_4$, 0.1 M Tris pH 7.5 and 3% isopropanol. Crystals grew to full size within one week. Prior to data collection, crystals were cryoprotected by immersion with a cryo buffer composed of the respective reservoir solution containing 25% glycerol, and flash-frozen in liquid nitrogen.

Data Collection and Processing:

Diffraction data for 3a and 4b were collected with synchrotron radiation at the Advanced Photon Source (Argonne, Ill., USA). Dataset 3a was collected at beamline 24-ID-E with a wavelength of 0.97918 Å on an Eiger 16M detector at a temperature of 100 K. Dataset 4b was collected at beamline 24-ID-C with a wavelength of 0.97920 Å on an Pilatus 6M detector at 100 K. Dataset 4a was collected in-house on a Rigaku 007 HF+X-ray diffractometer equipped with a Cu rotating anode and a Saturn 944+ CCD detector at a wavelength of 1.54178 Å at 100 K. Indexing, integration and scaling of datasets 3a and 4b were performed with XDS (Kabsch, 2010, Acta Crystallogr. Sect. D Biol. Crystallogr. 66:125-132), whereas processing of dataset 4a was performed with HKL2000 (Otwinowski & Minor, 1997, Methods Enzymol. 276:307-326). Data collection and refinement statistics are given in Table 2.

Structure Determination and Refinement:

All three structures were determined by molecular replacement with the program PHASER (McCoy, et al., 2007, J. Appl. Crystallogr. 40:658-674) as included into CCP4i version 7.0.043 (Winn, et al., 2011, Acta Crystallogr. Sect. D Biol. Crystallogr. 67:235-242), applying a 1.9 Å crystal structure of MIF (PDB ID 3U18) with truncated flexible side chains as a search model (Bai, et al., 2012, J. Biol. Chem. 287:30653-30663). Crystal structure refinement was performed with PHENIXREFINE version 1.11.1-2575 (Adams, et al., 2010, Acta Crystallogr. Sect. D Biol. Crystallogr. 66:213-221), manual model building was performed with COOT (Emsley, et al., 2010, Acta Crystallogr. Sect. D Biol. Crystallogr. 66:486-501). A randomly chosen subset of 5% of the reflections was excluded from the refinement and used for the calculation of $R_{free}$. Initially, Cartesian simulated annealing (default temperatures) was performed, followed by refinement of x, y, z coordinates, occupancies and individual ADPs. Depending on the improvement of $R_{free}$, APDs were treated anisotropically (3a), with isotropic TLS groups (4b) or isotropically without the application of TLS groups (4a). TLS groups were identified by the TLSMD web server (Painter & Merritt, 2006, J. Appl. Crystallogr. 39:109-111). Refinement of the high-resolution crystal structure 3a was carried out with the addition of riding hydrogen atoms. SMILES codes of the ligands used for the generation of ligand restraints were generated with the MOLINSPIRATION web server (www dot molinspiration dot com). Restraints for 3a were generated with the GRADE web server (Smart, et al., GRADE, Version v1.102. www dot globalphasing dot com, 2011) and for 4a and 4b with PHENIXELBOW (Moriarty, et al., 2009, Acta Crystallogr., Sect. D Biol. Crystallogr. 65:1074-1080).

TABLE 2

Data collection and refinement statistics[a]

| | MIF-ligand complex (PDB code) | | |
|---|---|---|---|
| | 3a (6B1K) | 4a (6B1C) | 4b (6B2C) |
| (A) Data collection and processing | | | |
| Space group | I4$_1$22 | P3$_1$21 | P3$_1$21 |
| Unit cell parameters: a, b, c (Å) | 116.9, 116.9, 102.2 | 96.0, 96.0, 104.1 | 97.4, 97.4, 105.6 |
| Matthews coefficient (Å$^3$/Da)[b] | 2.3 | 2.3 | 2.3 |
| Solvent content (%)[b] | 47 | 47 | 47 |
| (B) Diffraction data | | | |
| Resolution range (Å) | 200.00-1.17 (1.23-1.17) | 50.00-2.16 (2.20-2.16) | 200.00-2.00 (2.12-2.00) |
| Unique reflections | 118139 (16818) | 28763/1067 | 38918/5897 |
| R(I)$_{sym}$ (%) | 5.8 (72.7) | 7.7 (45.8) | 7.7 (42.2) |
| Wilson B factor (Å$^2$) | 13.3 | 31.4 | 35.8 |
| Completeness (%) | 97.9 (86.8) | 95.8 (71.1) | 98.1 (93.1) |
| Multiplicity | 11.9 (8.1) | 5.2 (3.0) | 4.0 (3.9) |
| <I/σ(I)> | 19.2 (2.1) | 15.7 (2.3) | 9.0 (2.0) |
| (C) Refinement | | | |
| Resolution range (Å) | 82.66-1.17 | 38.59-2.16 | 65.92-2.00 |
| Reflections used in refinement (work/free) | 112092/5900 | 26610/1406 | 36969/1946 |
| Final R value for all reflections (work/free) (%) | 13.5/15.4 | 21.0/25.4 | 19.14/22.16 |
| Protein residues | 342 | 342 | 342 |
| Inhibitor atoms | 72 | 50 | 26 |
| Water molecules | 333 | 144 | 143 |
| RMSD, bond lengths (Å) | 0.008 | 0.008 | 0.008 |
| RMSD, bond angles (°) | 1.0 | 0.8 | 0.8 |
| Ramachandran plot:[c] | | | |
| Ramachandran favored (%) | 98.5 | 95.7 | 97.9 |
| Ramachandran outliers (%) | 0.0 | 0.0 | 0.0 |
| Mean B factors (Å$^2$): | | | |
| Protein non-hydrogen atoms | 15.1 | 30.4 | 40.9 |
| Inhibitor | 15.9 | 40.8 | 61.6 |
| Water molecules | 32.6 | 33.9 | 43.8 |

[a]Values in brackets refer to the highest resolution shell
[b]Matthews coefficient and solvent content were calculated with the Matthews_coef program from the CCP4 suite (Winn, et al., 2011, Acta Crystallogr. Sect. D Biol. Crystallogr. 67: 235-242)
[c]Ramachandran plots were calculated with MolProbity (Chen, et al., 2010, Acta Crystallogr. Sect. D Biol. Crystallogr. 66: 12-21)

Figure 7A:
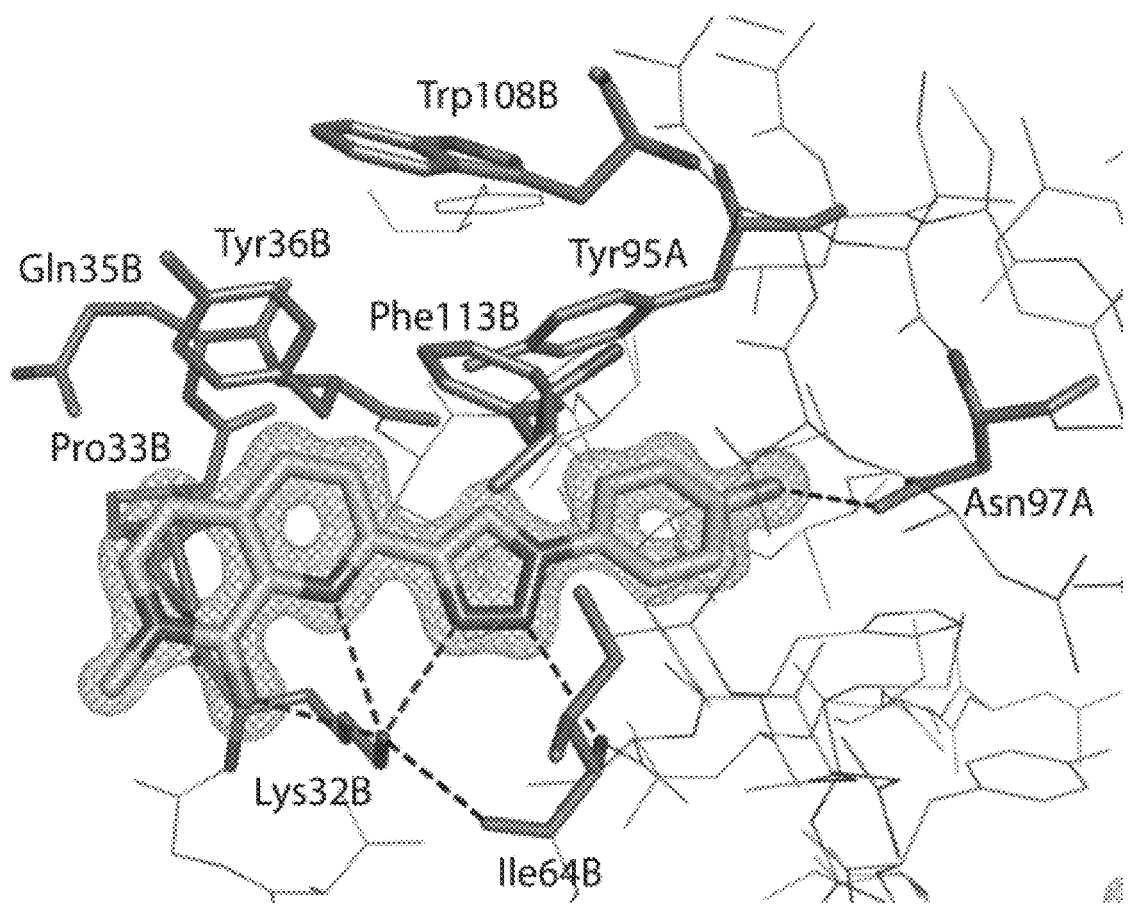
FIGS. 7A-7C illustrate OMIT maps of the inhibitors bound to the binding site at the interface of monomers A and B. The OMIT map is displayed as green mesh for (FIG. 7A) 3a (carbon atoms in light gray) (contour level 4.0 σ), (FIG. 7B) 4a (carbon atoms in light gray) (contour level 2.5 σ), and (FIG. 7C) 4b (contour level 3.0 σ). Hydrogen bonds discussed in the main text are indicated as black dotted lines.
Figure 7B:
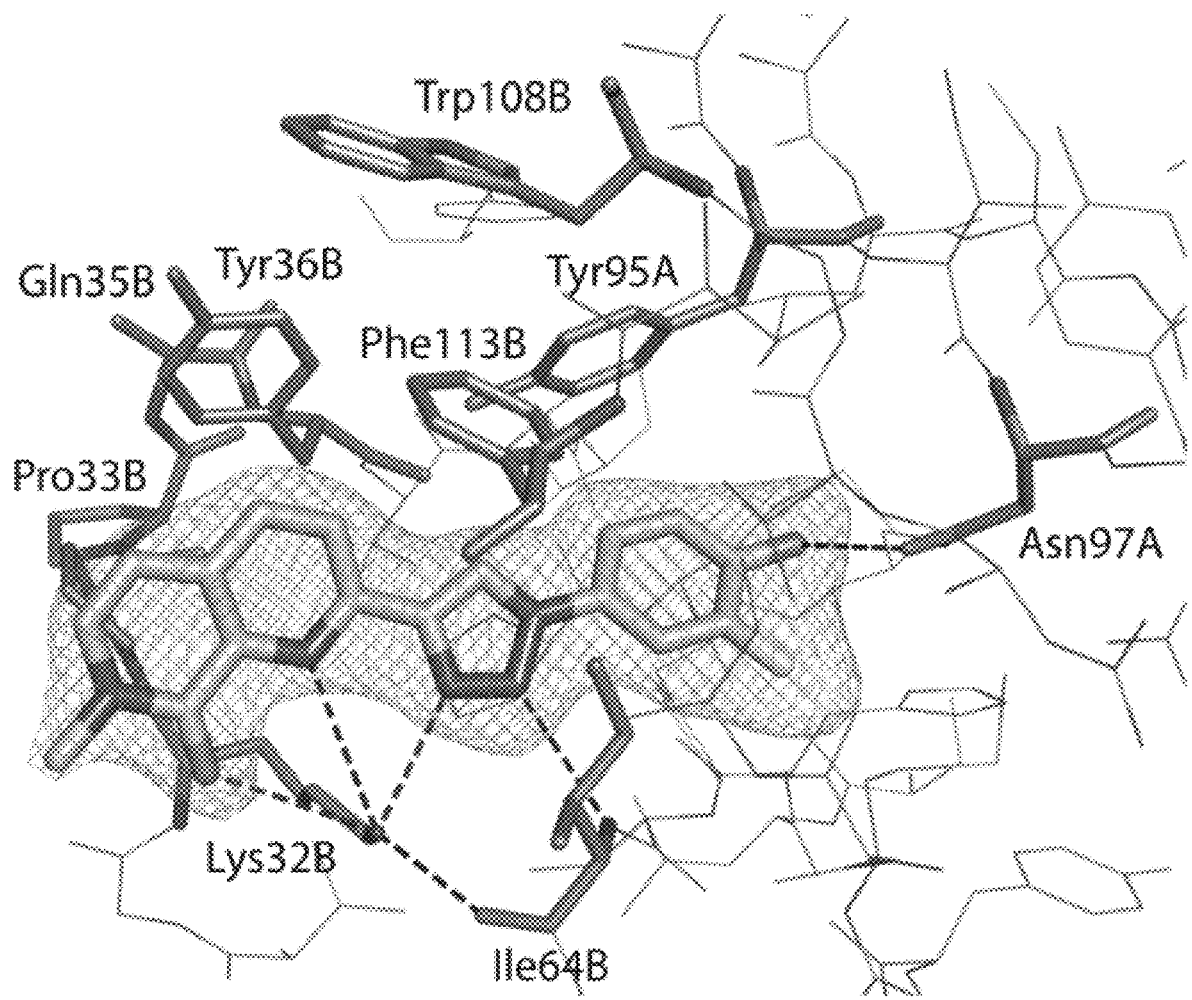
Figure 7C:
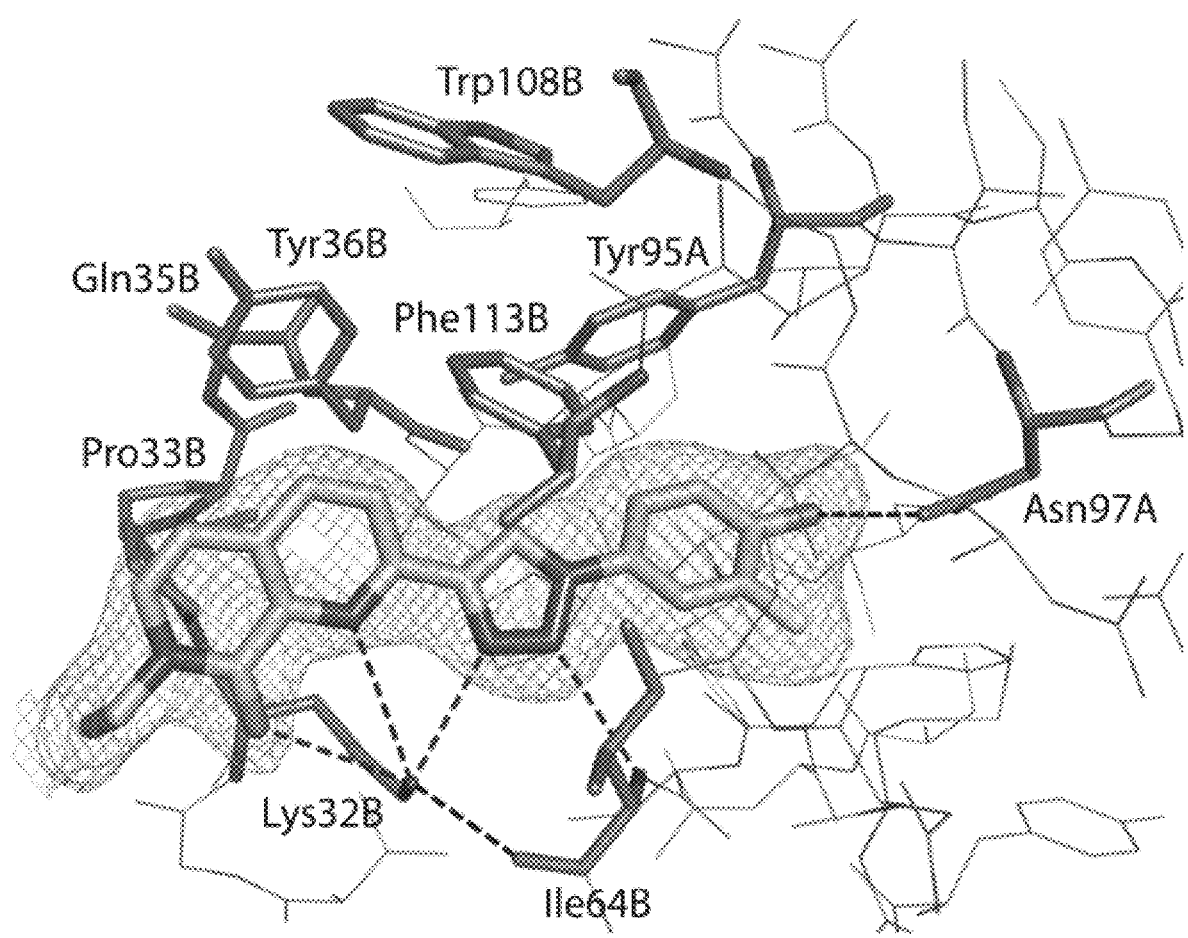

Description of the Ligand Binding Sites:

Only the crystal packing of MIF co-crystallized with 3a (space group I4$_1$22) enables three copies of the ligand to bind simultaneously. In the space group P3$_1$21 as a result of the co-crystallization with 4a and 4b, the binding site at the interface of monomers B and C is blocked due to the packing in the crystal. Furthermore, likewise due to crystal packing, 4b is not able to occupy the binding site at the interface of monomers A and C due to its larger size compared to 4a. At the latter binding site, only a partially defined and diffuse electron density—not sufficient for ligand modelling—is observed. FIG. 7 shows the polder OMIT maps (Liebschner, et al., 2017, Acta Crystallogr. Sect. D Struct. Biol. 73:148-157) of all three ligands bound to the binding site established by monomers A and B. Both oxygens of the solvent-exposed terminal carboxy group of 4b could not be reliably detected in the electron density and thus were not included into the model. This can, in one aspect, be explained by high flexibility of the solubilizing moiety sticking out of the pocket and into the solvent.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I), or a salt, solvate, enantiomer, or diastereoisomer thereof:

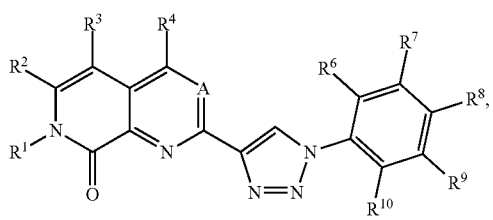

(I)

wherein:

A is $CR^5$ or N;

$R^1$ is:
(a) methyl substituted with at least one selected from the group consisting of —C(=O)R, —C(=O)OR, —C(=O)NRR, —OC(=O)R, —OC(=O)OR, and —OC(=O)NRR; or
(b) selected from the group consisting of propyl, isopropyl, butyl, isobutyl, tert butyl, pentyl, neopentyl, hexyl, cyclopropylmethyl, and $C_1$-$C_6$ heteroalkyl; or
(c) selected from the group consisting of ethyl, propyl, isopropyl, butyl, isobutyl, tert butyl, pentyl, neopentyl, hexyl, and cyclopropylmethyl, and $C_1$-$C_6$ heteroalkyl, wherein the ethyl, propyl, isopropyl, butyl, isobutyl, tert butyl, pentyl, neopentyl, hexyl, cyclopropylmethyl or heteroalkyl group is substituted with at least one selected from the group consisting of —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR, $R^2$ and $R^3$ are independently selected from the group consisting of H, halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, ($C_3$-$C_7$ cycloalkyl)-$C_1$-$C_4$ alkylene, ($C_6$-$C_{10}$ aryl)-$C_1$-$C_4$ alkylene, (5-10 membered heteroaryl)-$C_1$-$C_4$ alkylene, (4-10 membered heterocyclyl)-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR;

or one of $R^2$ and $R^3$ is -L-$R^{11}$, wherein:

L is selected from the group consisting of a bond, —O—, —N(R)—, $C_1$-$C_4$ alkylene, —C(=O)—, —N(R)C(=O)—, and —C(=O)N(R)—; and $R^{11}$ is optionally substituted phenyl, pyridinyl, or pyrimidinyl;

$R^4$, $R^5$, $R^6$, and $R^{10}$ are each independently selected from the group consisting of H, halogen, $C_1$-$C_6$ alkyl, and $C_1$-$C_6$ haloalkyl;

$R^7$, $R^8$, and $R^9$ are independently selected from the group consisting of H, halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, ($C_3$-$C_7$ cycloalkyl)-$C_1$-$C_4$ alkylene, ($C_6$-$C_{10}$ aryl)-$C_1$-$C_4$ alkylene, (5-10 membered heteroaryl)-$C_1$-$C_4$ alkylene, (4-10 membered heterocyclyl)-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR;

each occurrence of R is independently selected from the group consisting of H, $C_1$-$C_6$ alkyl, $C_2$-$C_6$ alkenyl, $C_2$-$C_6$ alkynyl, $C_3$-$C_8$ cycloalkyl, or $C_3$-$C_8$ heterocyclyl, or the two R bound to the same N optionally form a $C_3$-$C_8$ heterocyclyl group;

each occurrence of R' is independently selected from the group consisting of $C_1$-$C_6$ alkyl, $C_2$-$C_6$ alkenyl, $C_2$-$C_6$ alkynyl, $C_3$-$C_8$ cycloalkyl, or $C_3$-$C_5$ heterocyclyl;

each alkyl, alkenyl, alkynyl, cycloalkyl, or heterocyclyl group is optionally substituted with at least one substituent selected from the group consisting of halogen, $C_6$-$C_{10}$ aryl, 5-10 membered heteroaryl, 4-10 membered heterocyclyl, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR; and each phenyl or heteroaryl group is optionally substituted with at least one substituent selected from the group consisting of halogen, $C_1$-$C_6$ alkyl, $C_2$-$C_6$ alkenyl, $C_2$-$C_6$ alkynyl, $C_3$-$C_7$ cycloalkyl, $C_6$-$C_{10}$ aryl, 5-10 membered heteroaryl, 4-10 membered heterocyclyl, $C_3$-$C_7$ cycloalkyl-$C_1$-$C_4$ alkylene, $C_6$-$C_{10}$ aryl-$C_1$-$C_4$ alkylene, 5-10 membered heteroaryl-$C_1$-$C_4$ alkylene, 4-10 membered heterocyclyl-$C_1$-$C_4$ alkylene, nitro, —CN, —OR, —NRR, —C(=O)R, —C(=O)OR, —C(=O)NRR, —OC(=O)R, —OC(=O)OR, —OC(=O)NRR, —N(R)C(=O)R, —N(R)C(=O)OR, —N(R)C(=O)NRR, —SR, —S(=O)R', —S(=O)$_2$R', and —S(=O)$_2$NRR.

2. The compound of claim 1, which is selected from the group consisting of:

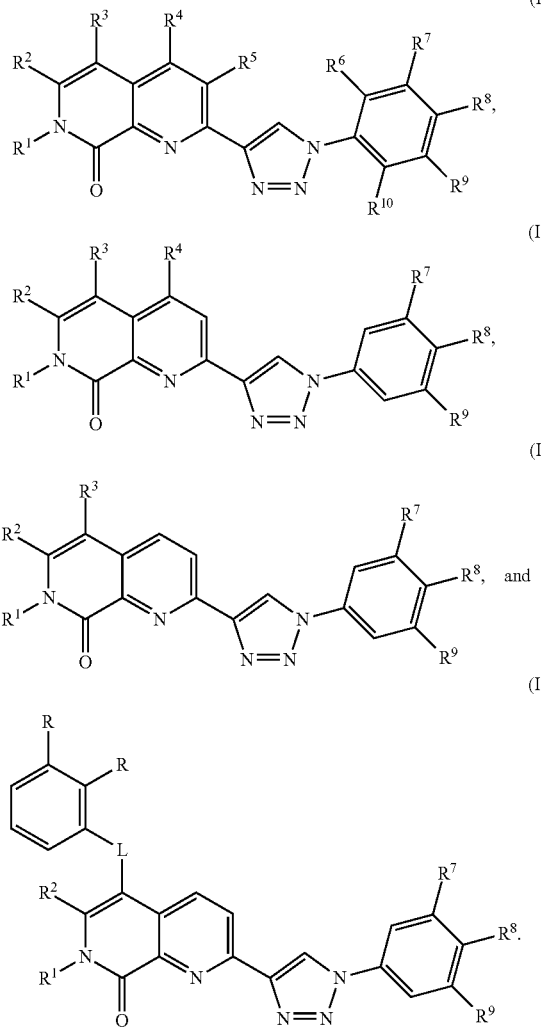

3. The compound of claim 1, wherein $R^1$ is selected from the group consisting of —CH$_2$CH$_2$OH, —CH$_2$CH$_2$NH$_2$, —CH$_2$CH$_2$OCH$_2$CH$_2$OH, —CH$_2$CH$_2$OCH$_2$CH$_2$NH$_2$, —CH$_2$CH$_2$OCH$_2$CH$_2$-4-morpholinyl, —CH$_2$COOH, —CH$_2$CH$_2$COOH, and —CH$_2$CH$_2$CH$_2$COOH.

4. The compound of claim 1, wherein $R^2$ is H or —OR.

5. The compound of claim 1, wherein $R^3$ is selected from the group consisting of H, $C_6$-$C_{10}$ aryl, and —OR.

6. The compound of claim 1, wherein $R^3$ is H, unsubstituted phenyl, or phenyl substituted with 1 substituent selected from the group consisting of $C_1$-$C_6$ alkyl, halogen, $C_1$-$C_6$ alkoxy, and —OR", wherein R" is unsubstituted phenyl or phenyl substituted with 1 group independently selected from the group consisting of —OR and —C(=O)OR.

7. The compound of claim 1, wherein one of $R^2$ and $R^3$ is -L-$R^{11}$.

8. The compound of claim 1, wherein L is O or NH.

9. The compound of claim 1, wherein $R^2$ and an optional substituent in $R^{11}$ are independently selected from the group consisting of H, $C_1$-$C_6$ alkoxy, $C_1$-$C_6$ alkoxy-$C_1$-$C_6$ alkyl, carboxy, carboxy-$C_1$-$C_6$ alkyl, amino-$C_1$-$C_6$ alkyl, $C_1$-$C_6$ alkylamino-$C_1$-$C_6$ alkyl, di($C_1$-$C_6$ alkyl)amino-$C_1$-$C_6$ alkyl, amino-$C_1$-$C_6$ alkoxy-$C_1$-$C_6$ alkyl, $C_1$-$C_6$ alkylamino-$C_1$-$C_6$ alkoxy-$C_1$-$C_6$ alkyl, di($C_1$-$C_6$ alkyl)amino-$C_1$-$C_6$ alkoxy-$C_1$-$C_6$ alkyl, 4-10 membered heterocyclyl-$C_1$-$C_6$ alkyl, 4-10 membered heterocyclyl-$C_1$-$C_6$ alkoxy-$C_1$-$C_6$ alkyl, $C_1$-$C_6$ alkoxy-$C_1$-$C_6$ alkoxy, amino-$C_1$-$C_6$ alkoxy, $C_1$-$C_6$ alkylamino-$C_1$-$C_6$ alkoxy, di($C_1$-$C_6$ alkyl)amino-$C_1$-$C_6$ alkoxy, amino-$C_1$-$C_6$ alkoxy-$C_1$-$C_6$ alkoxy, $C_1$-$C_6$ alkylamino-$C_1$-$C_6$ alkoxy-$C_1$-$C_6$ alkoxy, di($C_1$-$C_6$ alkyl)amino-$C_1$-$C_6$ alkoxy-$C_1$-$C_6$ alkoxy, 4-10 membered heterocyclyl-$C_1$-$C_6$ alkoxy, 4-10 membered heterocyclyl-$C_1$-$C_6$ alkoxy, carboxy-$C_1$-$C_6$ alkoxy, carboxy-$C_1$-$C_6$ alkyl-$C_1$-$C_6$ alkoxy, and carboxy-$C_1$-$C_6$ alkoxy-$C_1$-$C_6$ alkoxy.

10. The compound of claim 1, wherein $R^4$ and $R^5$ are independently selected from the group consisting of H, F, and $C_1$-$C_6$ alkyl.

11. The compound of claim 1, wherein $R^6$ is H; $R^7$ is halogen, $C_1$-$C_6$ alkyl, or —OR; $R^8$ is —OH, halogen, —CN, —OR, —NRR, or —C(=O)NRR; $R^9$ is H or halogen; and $R^{10}$ is H.

12. The compound of claim 1, wherein $R^6$, $R^7$, $R^9$, and $R^{10}$ are each independently selected from the group consisting of H and F.

13. The compound of claim 1, wherein R' is selected from the group consisting of H, F, Cl, and —OH.

14. A pharmaceutical composition comprising at least one compound of claim 1 and at least one pharmaceutically acceptable excipient.

* * * * *